United States Patent
Mizori et al.

(10) Patent No.: US 8,513,375 B2
(45) Date of Patent: *Aug. 20, 2013

(54) IMIDE-LINKED MALEIMIDE AND POLYMALEIMIDE COMPOUNDS

(75) Inventors: Farhad G Mizori, San Diego, CA (US); Stephen M Dershem, San Diego, CA (US)

(73) Assignee: Designer Molecules, Inc.

( * ) Notice: Subject to any disclaimer, the term of this patent is extended or adjusted under 35 U.S.C. 154(b) by 126 days.

This patent is subject to a terminal disclaimer.

(21) Appl. No.: 13/021,700

(22) Filed: Feb. 4, 2011

(65) Prior Publication Data

US 2011/0130485 A1    Jun. 2, 2011

Related U.S. Application Data

(63) Continuation-in-part of application No. 11/786,029, filed on Apr. 11, 2007, now Pat. No. 7,884,174, which is a continuation-in-part of application No. 10/835,911, filed on Apr. 30, 2004, now Pat. No. 7,208,566.

(60) Provisional application No. 61/358,901, filed on Jun. 26, 2010, provisional application No. 60/468,037, filed on May 5, 2003.

(51) Int. Cl.
*C08G 69/08* (2006.01)
*C08G 73/10* (2006.01)
*C08G 73/14* (2006.01)

(52) U.S. Cl.
USPC ............. 528/310; 528/322; 528/27; 548/433; 548/461; 548/475

(58) Field of Classification Search
USPC ......... 548/434, 400, 433, 461, 475; 528/310, 528/322, 27; 525/282
See application file for complete search history.

(56) References Cited

U.S. PATENT DOCUMENTS

| | | |
|---|---|---|
| 3,901,845 A | 8/1975 | Newbould |
| 3,905,820 A | 9/1975 | Frass |
| 4,075,167 A | 2/1978 | Takamizawa et al. |
| 4,111,879 A | 9/1978 | Mori et al. |
| 4,224,216 A | 9/1980 | Locatelli et al. |
| 4,675,379 A | 6/1987 | Mikroyannidis et al. |

(Continued)

FOREIGN PATENT DOCUMENTS

| | | |
|---|---|---|
| CN | 1187507 A | 7/1998 |
| EP | 0488066 A1 | 6/1992 |

(Continued)

OTHER PUBLICATIONS

Andersson et al., "Initiator-Free Photopolymerization of an Aliphatic Vinyl Ether-Maleimide Monomer", J Coatings Tech 69:91-95, 1997.
Callais et al., "New Polymerization Technologies for Advanced Materials", Arkema, Inc. Presentation (King of Prussia, PA), Dec. 20, 2007.

(Continued)

*Primary Examiner* — Duc Truong
(74) *Attorney, Agent, or Firm* — The Law Office of Jane K. Babin, Professional Corporation; Jane K. Babin

(57) ABSTRACT

The invention is directed to maleimide thermosets incorporating imide-extended mono-, bis-, or polymaleimide compounds. These imide-extended maleimide compounds are prepared by the condensation of appropriate anhydrides with appropriate diamines to give amine terminated compounds. These compounds are then condensed with excess maleic anhydride to yield imide-extended maleimide compounds.

10 Claims, 4 Drawing Sheets

(56) References Cited

U.S. PATENT DOCUMENTS

| | | |
|---|---|---|
| 4,775,740 A | 10/1988 | Beggs et al. |
| 4,925,915 A | 5/1990 | Mueller et al. |
| 4,931,540 A | 6/1990 | Mueller et al. |
| 4,968,738 A | 11/1990 | Dershem |
| 5,045,127 A | 9/1991 | Dershem et al. |
| 5,064,480 A | 11/1991 | Dershem et al. |
| 5,189,116 A | 2/1993 | Boyd et al. |
| 5,229,485 A | 7/1993 | Kramer et al. |
| 5,232,962 A | 8/1993 | Dershem et al. |
| 5,284,959 A | 2/1994 | Marien et al. |
| 5,306,333 A | 4/1994 | Dershem et al. |
| 5,358,992 A | 10/1994 | Dershem et al. |
| 5,393,887 A | 2/1995 | Petit |
| 5,403,389 A | 4/1995 | Dershem |
| 5,447,988 A | 9/1995 | Dershem et al. |
| 5,489,641 A | 2/1996 | Dershem |
| 5,554,769 A | 9/1996 | Sheppard et al. |
| 5,602,205 A | 2/1997 | Singh et al. |
| 5,616,666 A | 4/1997 | Morton et al. |
| 5,646,241 A | 7/1997 | Dershem et al. |
| 5,717,034 A | 2/1998 | Dershem et al. |
| 5,718,941 A | 2/1998 | Dershem et al. |
| 5,753,748 A | 5/1998 | Dershem et al. |
| 5,760,165 A | 6/1998 | Dao et al. |
| 5,770,681 A | 6/1998 | Corley |
| 5,861,111 A | 1/1999 | Dershem et al. |
| 5,891,566 A | 4/1999 | Sakumoto et al. |
| 5,969,036 A | 10/1999 | Dershem |
| 5,973,166 A | 10/1999 | Mizori et al. |
| 6,034,194 A | 3/2000 | Dershem |
| 6,034,195 A | 3/2000 | Dershem |
| 6,063,828 A | 5/2000 | Ma et al. |
| 6,121,358 A | 9/2000 | Dershem et al. |
| 6,187,886 B1 | 2/2001 | Husson, Jr. et al. |
| 6,211,320 B1 | 4/2001 | Dershem et al. |
| 6,214,923 B1 | 4/2001 | Goto et al. |
| 6,265,530 B1 | 7/2001 | Herr et al. |
| 6,281,314 B1 | 8/2001 | Tong et al. |
| 6,300,456 B1 | 10/2001 | Musa |
| 6,303,743 B1 | 10/2001 | You et al. |
| 6,316,566 B1 | 11/2001 | Ma et al. |
| 6,355,750 B1 | 3/2002 | Herr |
| 6,423,780 B1 | 7/2002 | Dershem et al. |
| 6,429,281 B1 | 8/2002 | Dershem et al. |
| 6,521,731 B2 | 2/2003 | Dershem et al. |
| 6,620,946 B2 | 9/2003 | Dershem et al. |
| 6,699,929 B2 | 3/2004 | Musa et al. |
| 6,730,763 B1 | 5/2004 | Okazaki et al. |
| 6,743,852 B2 | 6/2004 | Dershem et al. |
| 6,790,597 B2 | 9/2004 | Dershem |
| 6,825,245 B2 | 11/2004 | Dershem |
| 6,831,132 B2 | 12/2004 | Liu et al. |
| 6,852,814 B2 | 2/2005 | Dershem et al. |
| 6,881,820 B1 | 4/2005 | Meador et al. |
| 6,916,856 B2 | 7/2005 | Dershem |
| 6,946,523 B2 | 9/2005 | Dershem et al. |
| 6,960,636 B2 | 11/2005 | Dershem et al. |
| 6,963,001 B2 | 11/2005 | Dershem et al. |
| 6,977,057 B2 | 12/2005 | Reitz et al. |
| 7,102,015 B2 | 9/2006 | Dershem et al. |
| 7,157,587 B2 | 1/2007 | Mizori et al. |
| 7,176,044 B2 | 2/2007 | Forray et al. |
| 7,208,566 B2 | 4/2007 | Mizori et al. |
| 7,285,613 B2 | 10/2007 | Dershem et al. |
| 7,309,724 B2 | 12/2007 | Dershem et al. |
| 7,517,925 B2 | 4/2009 | Dershem et al. |
| 7,678,879 B2 | 3/2010 | Dershem |
| 7,777,064 B2 | 8/2010 | Mizori |
| 7,786,234 B2 | 8/2010 | Dershem et al. |
| 7,786,248 B2 | 8/2010 | Dershem |
| 7,795,362 B2 | 9/2010 | Dershem |
| 7,868,113 B2 | 1/2011 | Dershem |
| 7,875,688 B2 | 1/2011 | Dershem et al. |
| 7,884,174 B2 | 2/2011 | Mizori et al. |
| 7,928,153 B2 | 4/2011 | Dershem |
| 8,008,419 B2 | 8/2011 | Dershem |
| 8,013,104 B2 | 9/2011 | Dershem |
| 8,039,663 B2 | 10/2011 | Dershem |
| 8,043,534 B2 | 10/2011 | Dershem |
| 2002/0062923 A1 | 5/2002 | Forray |
| 2002/0099168 A1 | 7/2002 | Dershem et al. |
| 2002/0188137 A1 | 12/2002 | Dershem et al. |
| 2002/0193541 A1 | 12/2002 | Dershem et al. |
| 2002/0198356 A1 | 12/2002 | Dershem et al. |
| 2003/0008992 A1 | 1/2003 | Dershem et al. |
| 2003/0055121 A1 | 3/2003 | Dershem et al. |
| 2003/0060531 A1 | 3/2003 | Dershem et al. |
| 2003/0087999 A1 | 5/2003 | Dershem et al. |
| 2003/0109666 A1 | 6/2003 | Dershem et al. |
| 2003/0125551 A1 | 7/2003 | Dershem et al. |
| 2003/0208016 A1 | 11/2003 | Dershem et al. |
| 2004/0019224 A1 | 1/2004 | Dershem et al. |
| 2004/0077798 A1 | 4/2004 | Dershem et al. |
| 2004/0082724 A1 | 4/2004 | Dershem et al. |
| 2004/0102566 A1 | 5/2004 | Forray et al. |
| 2004/0123948 A1 | 7/2004 | Dershem et al. |
| 2004/0225026 A1 | 11/2004 | Mizori et al. |
| 2004/0225045 A1 | 11/2004 | Forray |
| 2004/0225059 A1 | 11/2004 | Mizori et al. |
| 2005/0136620 A1 | 6/2005 | Dershem et al. |
| 2005/0137277 A1 | 6/2005 | Dershem et al. |
| 2005/0267254 A1 | 12/2005 | Mizori et al. |
| 2005/0272888 A1 | 12/2005 | Dershem et al. |
| 2006/0009578 A1 | 1/2006 | Dershem |
| 2006/0063014 A1 | 3/2006 | Forray |
| 2006/0069232 A1 | 3/2006 | Dershem |
| 2006/0142517 A1 | 6/2006 | Dershem |
| 2007/0155869 A1 | 7/2007 | Dershem et al. |
| 2007/0205399 A1 | 9/2007 | Mizori |
| 2007/0299154 A1 | 12/2007 | Dershem et al. |
| 2008/0017308 A1 | 1/2008 | Dershem et al. |
| 2008/0075961 A1 | 3/2008 | Mizori |
| 2008/0075963 A1 | 3/2008 | Dershem |
| 2008/0075965 A1 | 3/2008 | Dershem |
| 2008/0103240 A1 | 5/2008 | Dershem |
| 2008/0142158 A1 | 6/2008 | Dershem |
| 2008/0146738 A1 | 6/2008 | Dershem |
| 2008/0160315 A1 | 7/2008 | Forray et al. |
| 2008/0191173 A1 | 8/2008 | Dershem et al. |
| 2008/0210375 A1 | 9/2008 | Dershem et al. |
| 2008/0251935 A1 | 10/2008 | Dershem |
| 2008/0257493 A1 | 10/2008 | Dershem |
| 2008/0262191 A1 | 10/2008 | Mizori |
| 2009/0061244 A1 | 3/2009 | Dershem |
| 2009/0215940 A1 | 8/2009 | Dershem |
| 2009/0288768 A1 | 11/2009 | Dershem |
| 2010/0041803 A1 | 2/2010 | Dershem |
| 2010/0041823 A1 | 2/2010 | Dershem |
| 2010/0041832 A1 | 2/2010 | Dershem |
| 2010/0041845 A1 | 2/2010 | Dershem et al. |
| 2010/0056671 A1 | 3/2010 | Dershem |
| 2010/0063184 A1 | 3/2010 | Dershem |
| 2010/0113643 A1 | 5/2010 | Dershem |
| 2010/0144977 A1 | 6/2010 | Dershem |
| 2010/0249276 A1 | 9/2010 | Dershem |
| 2011/0017400 A1 | 1/2011 | Dershem |
| 2011/0152466 A1 | 6/2011 | Dershem |

FOREIGN PATENT DOCUMENTS

| | | |
|---|---|---|
| JP | 62-212390 A | 9/1987 |
| JP | H01-135765 A2 | 5/1989 |
| JP | H01-167332 A | 7/1989 |
| JP | H02-639 A | 1/1990 |
| JP | H02-124940 A | 5/1990 |
| JP | H03-502941 A | 7/1991 |
| JP | H04-351634 A | 12/1992 |
| JP | H05-506255 A | 12/1992 |
| JP | H10-505599 | 6/1998 |
| JP | H10-505599 A | 6/1998 |
| JP | 11246759 A | 9/1999 |
| JP | 2001-100215 A | 4/2001 |
| WO | 8604073 A1 | 7/1986 |
| WO | 9003405 A1 | 4/1990 |
| WO | 9011317 A1 | 10/1990 |

| | | |
|---|---|---|
| WO | WO-9607691 | 3/1996 |
| WO | WO-2004099331 | 11/2004 |
| WO | WO-2005121190 | 12/2005 |
| WO | WO-2007100329 | 9/2007 |
| WO | WO-2008077140 | 6/2008 |
| WO | WO-2008077141 | 6/2008 |
| WO | WO-2008092168 | 7/2008 |
| WO | WO-2008124797 | 10/2008 |
| WO | WO-2008130894 | 10/2008 |
| WO | WO-2009117729 | 9/2009 |
| WO | WO-2010019832 | 2/2010 |

OTHER PUBLICATIONS

Chen et al., "Interfacial Properties of Metal/Polyimide Layered Strucutres", In Micro Electronic Packaging Technology—Materials and Processes (Shieh ed; ASM International, Metals Park, Ohio), pp. 345-350, 1989.

Fouassier, "Photoinitiation, Photopolymerization, and Photocuring", Hanser/Gardner, pp. 276-283, 1995.

Kohli, et al., "Co-Polymerization of Maleimides and Vinyl Ethers: A Structural Study", Macromolecules 31:5681-5689, 1998.

IMIDE-LINKED MALEIMIDE AND POLYMALEIMIDE COMPOUNDS

RELATED APPLICATIONS

This application claims the benefit of priority under 35 USC §119 of U.S. Provisional Application Ser. No. 61/358, 901 filed Jun. 26, 2010, and is also a Continuation-in-Part of Ser. No. 11/786,029, filed Apr. 11, 2007 (now U.S. Pat. No. 7,884,174; issued Feb. 8, 2011), which is in turn a Continuation-in-Part of Ser. No. 10/835,911, filed Apr. 30, 2004 (now U.S. Pat. No. 7,208,566; issued Apr. 24, 2007); which in turn claims priority to 60/468,037, filed May 5, 2003 (expired) the disclosures of which are incorporated herein by reference in their entireties.

FIELD OF THE INVENTION

The present invention relates to thermosetting adhesive compositions, methods of preparation and uses therefor. In particular, the present invention relates to thermosetting compounds and compositions containing imide-extended mono-, bis-, and polymaleimide compounds.

BACKGROUND OF THE INVENTION

Adhesive compositions, particularly conductive adhesives, are used for a variety of purposes in the fabrication and assembly of semiconductor packages and microelectronic devices. The more prominent uses include bonding of electronic elements such as integrated circuit chips to lead frames or other substrates, and bonding of circuit packages or assemblies to printed wire boards. Adhesives useful for electronic packaging applications typically exhibit properties such as good mechanical strength, curing properties that do not affect the component or the carrier, and thixotropic properties compatible with application to microelectronic and semiconductor components.

The bismaleimides represent one useful class of thermoset compounds that have been used in the microelectronic packaging industry. Bismaleimides are curable, meaning that they are capable of polymerization to yield cross-linked resins. In addition, bismaleimides may be homocured in the presence of free radicals or photoinitiators, or combined with other free-radical curing monomers (e.g., acrylates, methacrylates, syrenics, vinyl ethers, vinyl esters, allyl monomers, olefins, and the like). They may also be cured in the presence of comonomers via, Diels-Alder, -ene, and Michael addition mechanisms.

Commercially available bismaleimide thermoset compositions are noted for their high modulus, and excellent resistance to thermal degradation. However, these thermoset compositions are also well known for brittleness. The utility of the bismaleimide class of thermosets could be vastly improved if less brittle formulations could be achieved that retain the desirable thermal and elastic properties.

The imide-extended polymaleimides of this invention are contemplated for use in a wide variety of applications. They can be used, for example, as matrix resins and adhesives for aerospace, marine, automotive, wind turbine, and sports equipment composite products. They can be used in the fabrication of printed wiring boards and flexible circuits. The compounds of this invention can be used in die attach adhesives, underfill and mold compound resins for electronic packaging. They can be used to make thermally resistant films and film adhesives. They may also be used in the fabrication of anisotropic conductive adhesive films and pastes.

SUMMARY OF THE INVENTION

The invention is based on the discovery that a remarkable improvement in the performance of maleimide thermosets can be achieved through the incorporation of an imide-extended mono-, bis-, or polymaleimide compounds. These imide-extended maleimide compounds are readily prepared by the condensation of appropriate anhydrides with appropriate diamines to give amine terminated compounds. These compounds are then condensed with excess maleic anhydride to yield imide-extended maleimide compounds.

When incorporated into a thermoset composition, the imide-extended maleimide compounds described herein reduce brittleness and increase toughness in the composition, while not sacrificing thermal stability. The imide functional group is one of the most thermally stable groups known. Thus, the present invention provides a maleimide functionalized thermoset composition without thermally labile linkages, thereby providing superior thermal stability when used as a toughener.

In one embodiment, there are provided imide-extended bismaleimide compounds having the structure:

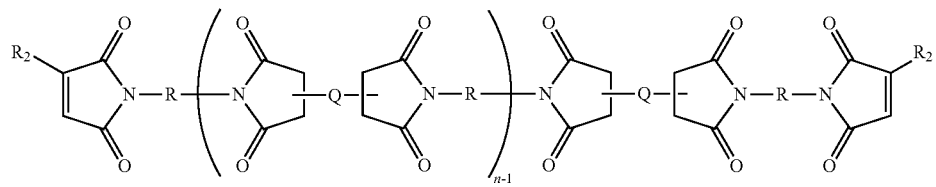

where each of R and Q is independently a substituted or an unsubstituted aliphatic, alkenyl, aromatic, heteroaromatic, or siloxane moiety; $R_2$ is H or methyl; and n is an integer having the value between 1 and about 10,
with the proviso that the imide-extended bismaleimide is not

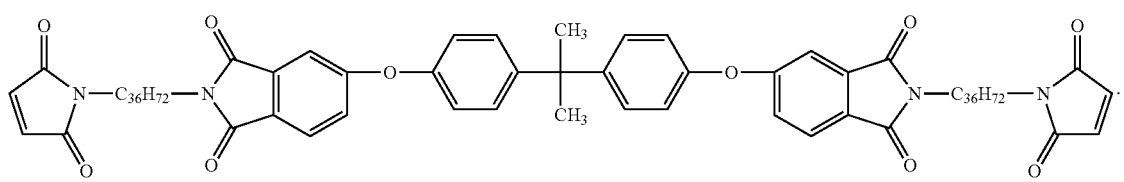

In another embodiment, there are provided monomaleimides having the structure:

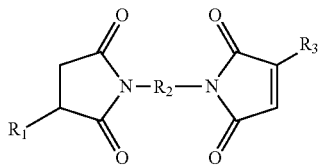

wherein $R_1$ is a substituted or an unsubstituted aliphatic, alkenyl, or aromatic moeity; $R_2$ is a substituted or an unsubstituted aliphatic, aromatic, or siloxane moiety; and $R_3$ is H or methyl.

In still another embodiment, there are provided polymaleimides including polymers including a plurality of pendant repeating units having the structure:

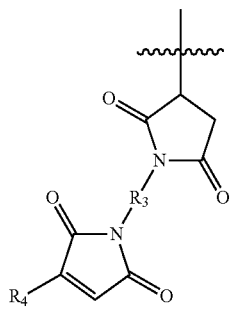

wherein $R_3$ is a substituted or an unsubstituted aliphatic, alkenyl, aromatic, heteroaromatic, or siloxane moiety; and $R_4$ is H or methyl In further embodiments, there are provided polymaleimides including polymers including a plurality of repeating units having the structure:

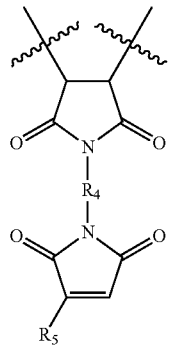

wherein $R_4$ is a substituted or an unsubstituted linear, branched, cyclic aliphatic, or alkenyl moiety having between 2 and about 500 carbon atoms, or a substituted or an unsubstituted aromatic moiety; $R_5$ is H or methyl.

In another embodiment, there are provided compounds having the structure:

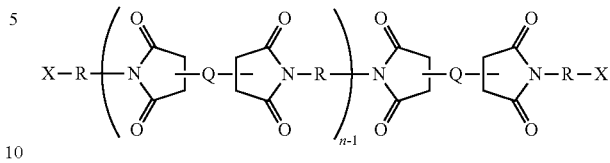

wherein each of R and Q is independently a substituted or an unsubstituted aliphatic, alkenyl, aromatic, heteroaromatic, or siloxane moiety; and X is a polymerizable moiety.

In another embodiment, there are provided adhesive compositions including at least one of the above-described monomaleimide, bismaleimide, or polymaleimide compounds, and at least one curing initiator.

In yet another embodiment, there are provided die-attach pastes including
a) 0.5 weight percent to about 98 weight percent (wt %) of at least one of the above described monomaleimide, bismaleimide, or polymaleimide compounds, or combinations thereof, based on total weight of the composition,
b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition.

In a further embodiment, there are provided methods for producing an imide-extended bismaleimide compound. Such methods can be performed, for example, by contacting a dianhydride with a diamine under conditions suitable to form an imide having terminal amino moieties; and contacting the terminal amino moieties with maleic anhydride under conditions suitable to form a maleimide, thereby producing an imide-extended bismaleimide monomer.

In another embodiment, there are provided assemblies including a first article permanently adhered to a second article by a cured aliquot of the die-attach paste according to the invention.

In yet another embodiment, there are provided kits for bonding an electronic component to a substrate comprising a package containing an amount of an adhesive composition comprising an imide-extended mono-, bis-, or polymaleimide sufficient to bond at least one electronic component to a substrate; and instructions for using the adhesive composition to bond the electronic component to the substrate.

In another embodiment, there are provided methods for producing a curable adhesive rope. Such a method can be performed, for example, by
a. providing an adhesive composition comprising an imide-extended mono-, bis- or polymaleimide; and
b. extruding the adhesive composition through a circular shaped form, thereby forming an adhesive rope.

BRIEF DESCRIPTION OF THE DRAWINGS

FIG. 3A shows a polymaleimide structure with succinimide connecting groups pendant from the maleimide polymer or oligomer. FIG. 3B shows a polymaleimide structure where the succinimide connecting groups are part of the main-chain maleimide polymer or oligomer.

DETAILED DESCRIPTION OF THE INVENTION

Figure 1:
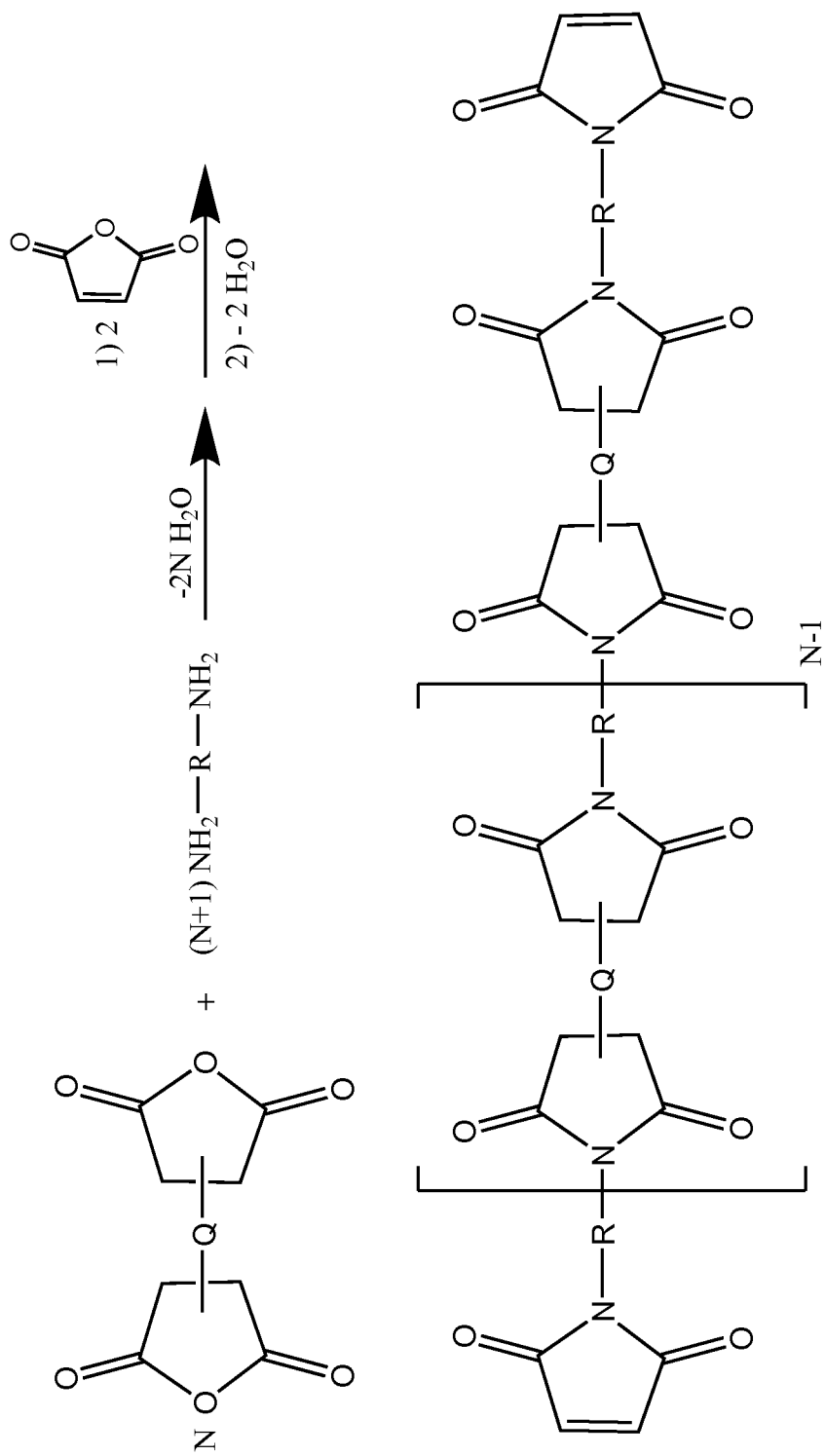
FIGS. 1 and 2 illustrate an exemplary preparation of an imide-extended compound of the invention.
Figure 2:
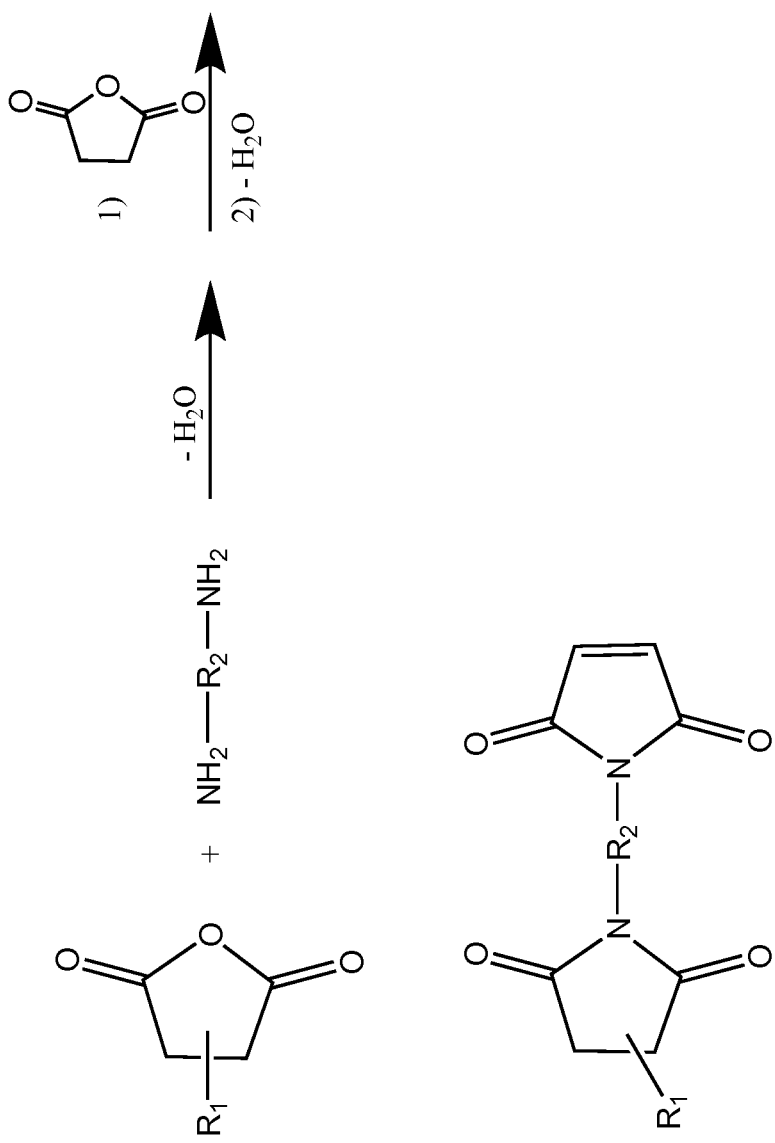

The present invention is based on the discovery that a remarkable improvement in the performance of maleimide thermosets can be achieved through the incorporation of imide-extended mono-, bis-, or polymaleimide compounds. In one embodiment, there are provided imide-extended bismaleimide compounds having the structure:

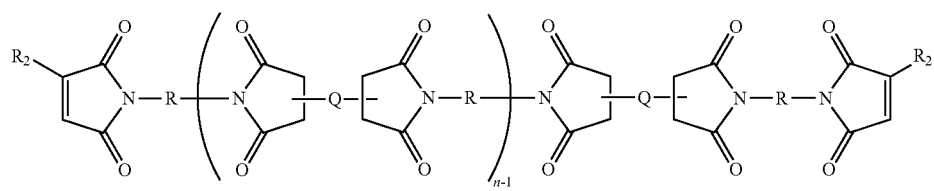

wherein each of R and Q is independently a substituted or an unsubstituted aliphatic, alkenyl, aromatic, heteroaromatic, or siloxane moiety; $R_2$ is H or methyl; and n is an integer having the value between 1 and about 10, with the proviso that the imide-extended bismaleimide is not

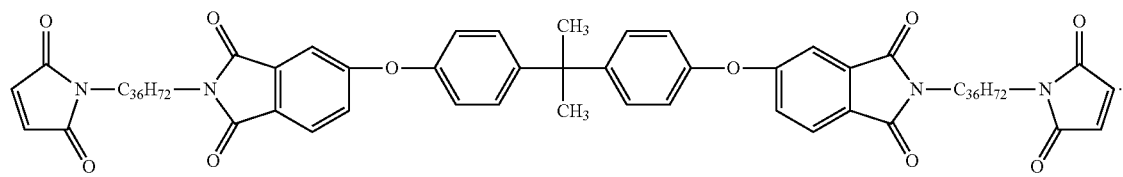

As used herein, the term "imide-extended" means that the compound contains at least one imide moiety in a non-terminal position of the molecule.

"Thermoplastic," as used herein, refers to the ability of a compound, composition or other material (e.g. a plastic) to dissolve in a suitable solvent or to melt to a liquid when heated and freeze to a solid state when cooled sufficiently.

"Thermoset," as used herein, refers to the ability of a compound, composition or other material to irreversibly "cure" resulting in a single tridimensional network that has greater strength and less solubility compared to the non-cured product. Thermoset materials are typically polymers that may be cured, for example, through heat (e.g. above 200° C.), via a chemical reaction (e.g. epoxy ring-opening, free-radical polymerization, etc. or through irradiation (e.g. visible light, UV light, electron beam radiation, ion-beam radiation, or X-ray irradiation).

Thermoset materials, such as thermoset polymers or resins, are typically liquid or malleable forms prior to curing, and therefore may be molded or shaped into their final form, and/or used as adhesives. Curing transforms the thermoset resin into a rigid infusible and insoluble solid or rubber by a cross-linking process. Thus, energy and/or catalysts are typically added that cause the molecular chains to react at chemically active sites (unsaturated or epoxy sites, for example), linking the polymer chains into a rigid, 3-D structure. The cross-linking process forms molecules with a higher molecular weight and resultant higher melting point. During the reaction, when the molecular weight of the polymer has increased to a point such that the melting point is higher than the surrounding ambient temperature, the polymer becomes a solid material.

"Cross-linking," as used herein, refers to the attachment of two or more oligomer or longer polymer chains by bridges of an element, a molecular group, a compound, or another oligomer or polymer. Crosslinking may take place upon heating or exposure to light; some crosslinking processes may also occur at room temperature or a lower temperature. As cross-linking density is increased, the properties of a material can be changed from thermoplastic to thermosetting.

As used herein, "B-stageable" refers to the properties of an adhesive having a first solid phase followed by a tacky rubbery stage at elevated temperature, followed by yet another solid phase at an even higher temperature. The transition from the tacky rubbery stage to the second solid phase is thermosetting. However, prior to thermosetting, the material behaves similarly to a thermoplastic material. Thus, such adhesives allow for low lamination temperatures while providing high thermal stability.

A "die" or "semiconductor die" as used herein, refers to a small block of semiconducting material, on which a functional circuit is fabricated.

A "flip-chip" semiconductor device is one in which a semiconductor die is directly mounted to a wiring substrate, such as a ceramic or an organic printed circuit board. Conductive terminals on the semiconductor die, usually in the form of solder bumps, are directly physically and electrically connected to the wiring pattern on the substrate without use of wire bonds, tape-automated bonding (TAB), or the like. Because the conductive solder bumps making connections to the substrate are on the active surface of the die or chip, the die is mounted in a face-down manner, thus the name "flip-chip."

"Underfill," "underfill composition" and "underfill material" are used interchangeably to refer to a material, typically polymeric compositions, used to fill gaps between a semiconductor component, such as a semiconductor die, and a substrate.

"Underfilling" refers to the process of applying an underfill composition to a semiconductor component-substrate interface, thereby filling the gaps between the component and the substrate.

The term "monomer" refers to a molecule that can undergo polymerization or copolymerization thereby contributing constitutional units to the essential structure of a macromolecule (a polymer).

"Polymer" and "polymer compound" are used interchangeably herein, to refer generally to the combined the products of a single chemical polymerization reaction. Polymers are produced by combining monomer subunits into a covalently bonded chain. Polymers that contain only a single type of monomer are known as "homopolymers," while polymers containing a mixture of monomers are known as "copolymers."

The term "copolymers" is inclusive of products that are obtained by copolymerization of two monomer species, those obtained from three monomers species (terpolymers), those obtained from four monomers species (quaterpolymers), etc. It is well known in the art that copolymers synthesized by chemical methods include, but are not limited to, molecules with the following types of monomer arrangements:

"alternating copolymers," which contain regularly alternating monomer residues;

"periodic copolymers," which have monomer residue types arranged in a repeating sequence;

"random copolymers," which have a random sequence of monomer residue types;

"statistical copolymers," which have monomer residues arranged according to a known statistical rule; and "block copolymers," which have two or more homopolymer subunits linked by covalent bonds. The blocks of homopolymer within block copolymers, for example, can be of any length and can be blocks of uniform or variable length. Block copolymers with two or three distinct blocks are called diblock copolymers and triblock copolymers, respectively; and "star copolymers," which have chains of monomer residues having different constitutional or configurational features that are linked through a central moiety.

The skilled artisan will appreciate that a single copolymer molecule may have different regions along its length that can be characterized as an alternating, periodic, random, etc. A copolymer product of a chemical polymerization reaction may contain individual polymeric fragments that each differ in the arrangement of monomer units. The skilled artisan will further be knowledgeable in methods for synthesizing each of these types of copolymers, and for varying reaction conditions to favor one type over another.

Furthermore, the length of a polymer chain according to the present invention, will typically vary over a range or average size produced by a particular reaction. The skilled artisan will be aware, for example, of methods for controlling the average length of a polymer chain produced in a given reaction and also of methods for size-selecting polymers after they have been synthesized.

Unless a more restrictive term is used, polymer is intended to encompass homopolymers, and copolymers having any arrangement of monomer subunits as well as copolymers containing individual molecules having more than one arrangement. With respect to length, unless otherwise indicated, any length limitations recited for the polymers described herein are to be considered averages of the lengths of the individual molecules in polymer.

"Thermoplastic elastomer" or "TPE", as used herein refers to a class of copolymers that consist of materials with both thermoplastic and elastomeric properties.

"Hard blocks" or "hard segments" as used herein refer to a block of a copolymer (typically a thermoplastic elastomer) that is hard at room temperature by virtue of a high melting point ($T_m$) or $T_g$. By contrast, "soft blocks" or "soft segments" have a $T_g$ below room temperature.

As used herein, "oligomer" or "oligomeric" refers to a polymer having a finite and moderate number of repeating monomers structural units. Oligomers of the invention typically have 2 to about 100 repeating monomer units; frequently 2 to about 30 repeating monomer units; and often 2 to about 10 repeating monomer units; and usually have a molecular weight up to about 3,000.

The skilled artisan will appreciate that oligomers and polymers may, depending on the availability of polymerizable groups or side chains, subsequently be incorporated as monomers in further polymerization or crosslinking reactions.

As used herein, "aliphatic" refers to any alkyl, alkenyl, cycloalkyl, or cycloalkenyl moiety.

"Aromatic hydrocarbon" or "aromatic" as used herein, refers to compounds having one or more benzene rings.

"Alkane," as used herein, refers to saturated straight-chain, branched or cyclic hydrocarbons having only single bonds. Alkanes have general formula $C_nH_{2n+2}$. "Cycloalkane," refers to an alkane having one or more rings in its structure.

As used herein, "alkyl" refers to straight or branched chain hydrocarbyl groups having from 1 up to about 500 carbon atoms. "Lower alkyl" refers generally to alkyl groups having 1 to 6 carbon atoms. The terms "alkyl" and "substituted alkyl" include, respectively, substituted and unsubstituted $C_1$-$C_{500}$ straight chain saturated aliphatic hydrocarbon groups, substituted and unsubstituted $C_2$-$C_{200}$ straight chain unsaturated aliphatic hydrocarbon groups, substituted and unsubstituted $C_4$-$C_{100}$ branched saturated aliphatic hydrocarbon groups, substituted and unsubstituted $C_1$-$C_{500}$ branched unsaturated aliphatic hydrocarbon groups.

For example, the definition of "alkyl" includes but is not limited to: methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tent-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, tricyclodecyl, adamantyl, norbornyl and the like.

In addition, as used herein "$C_{36}$" refers to all possible structural isomers of a 36 carbon aliphatic moiety, including branched isomers and cyclic isomers with up to three carbon-carbon double bonds in the backbone. One non-limiting example of a moiety that the definition of "$C_{36}$" refers to is the moiety comprising a cyclohexane-based core and four long "arms" attached to the core, as demonstrated by the following structure:

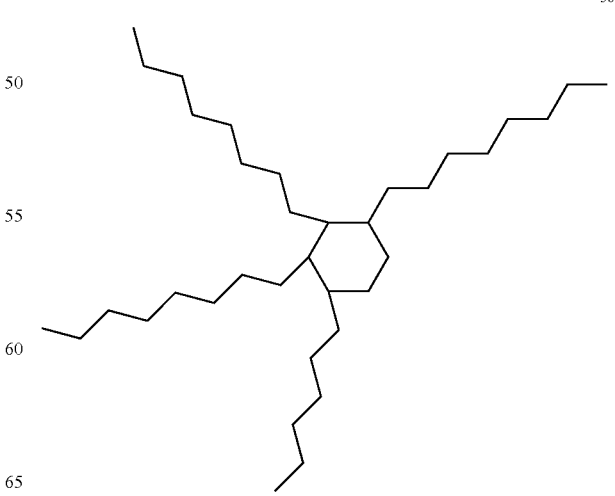

$C_{36}$

As used herein, "cycloalkyl" refers to cyclic ring-containing groups containing in the range of about 3 up to about 20 carbon atoms, typically 3 to about 15 carbon atoms. In certain embodiments, cycloalkyl groups have in the range of about 4 up to about 12 carbon atoms, and in yet further embodiments, cycloalkyl groups have in the range of about 5 up to about 8 carbon atoms, and "substituted cycloalkyl" refers to cycloalkyl groups further bearing one or more substituents as set forth below.

As used herein, the term "aryl" represents an unsubstituted, mono-, di- or trisubstituted monocyclic, polycyclic, biaryl aromatic groups covalently attached at any ring position capable of forming a stable covalent bond, certain preferred points of attachment being apparent to those skilled in the art (e.g., 3-phenyl, 4-naphtyl and the like). The aryl substituents are independently selected from the group consisting of halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy$C_{1-10}$alkyl, $C_{1-10}$alkylthio$C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino$C_{1-10}$alkyl, N-aryl-N—$C_{1-10}$alkylamino$C_{1-10}$alkyl, $C_{1-10}$alkylcarbonyl$C_{1-10}$alkyl, aryl $C_{1-10}$alkylcarbonyl $C_{1-10}$alkyl, $C_{1-10}$alkylcarboxy $C_{1-10}$alkyl, aryl$C_{1-10}$alkylcarboxy$C_{1-10}$alkyl, $C_{1-10}$alkylcarbonylamino$C_{1-10}$alkyl, and aryl$C_{1-10}$alkylcarbonylamino $C_{1-10}$alkyl.

Some specific examples of moieties encompassed by the definition of "aryl" include but are not limited to phenyl, biphenyl, naphthyl, dihydronaphthyl, tetrahydronaphthyl, indenyl, indanyl, azulenyl, anthryl, phenanthryl, fluorenyl, pyrenyl and the like. "Substituted aryl" refers to aryl groups further bearing one or more substituents as set forth below.

As used herein, "arylene" refers to a divalent aryl moiety. "Substituted arylene" refers to arylene moieties bearing one or more substituents as set forth above.

As used herein, "alkylaryl" refers to alkyl-substituted aryl groups and "substituted alkylaryl" refers to alkylaryl groups further bearing one or more substituents as set forth below.

As used herein, "arylalkyl" refers to aryl-substituted alkyl groups and "substituted arylalkyl" refers to arylalkyl groups further bearing one or more substituents as set forth below. Some examples of included but are not limited to (4-hydroxyphenyl)ethyl, or (2-aminonaphthyl) hexenyl.

As used herein, "arylalkenyl" refers to aryl-substituted alkenyl groups and "substituted arylalkenyl" refers to arylalkenyl groups further bearing one or more substituents as set forth below.

As used herein, "arylalkynyl" refers to aryl-substituted alkynyl groups and "substituted arylalkynyl" refers to arylalkynyl groups further bearing one or more substituents as set forth below.

As used herein, "aroyl" refers to aryl-carbonyl species such as benzoyl and "substituted aroyl" refers to aroyl groups further bearing one or more substituents as set forth below.

As used herein, "hetero" refers to groups or moieties containing one or more heteroatoms such as N, O, Si and S. Thus, for example "heterocyclic" refers to cyclic (i.e., ring-containing) groups having e.g. N, O, Si or S as part of the ring structure, and having in the range of 3 up to 14 carbon atoms. "Heteroaryl" and "heteroalkyl" moieties are aryl and alkyl groups, respectively, containing e.g. N, O, Si or S as part of their structure. The terms "heteroaryl", "heterocycle" or "heterocyclic" refer to a monovalent unsaturated group having a single ring or multiple condensed rings, from 1 to 8 carbon atoms and from 1 to 4 hetero atoms selected from nitrogen, sulfur or oxygen within the ring.

The definition of heteroaryl includes but is not limited to thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, pyrrolyl-2,5-dione, 3-pyrrolinyl, indolyl, isoindolyl, 3H-indolyl, indolinyl, indolizinyl, indazolyl, phthalimidyl (or isoindoly-1,3-dione), imidazolyl. 2H-imidazolinyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl, pyrrolidinyl-2,5-dione, imidazolidinyl-2,4-dione, 2-thioxo-imidazolidinyl-4-one, imidazolidinyl-2,4-dithione, thiazolidinyl-2,4-dione, 4-thioxo-thiazolidinyl-2-one, piperazinyl-2,5-dione, tetrahydro-pyridazinyl-3,6-dione, 1,2-dihydro-[1,2,4,5]tetrazinyl-3,6-dione, [1,2,4,5] tetrazinanyl-3,6-dione, dihydro-pyrimidinyl-2,4-dione, pyrimidinyl-2,4,6-trione, 1H-pyrimidinyl-2,4-dione, 5-iodo-1H-pyrimidinyl-2,4-dione, 5-chloro-1H-pyrimidinyl-2,4-dione, 5-methyl-1H-pyrimidinyl-2,4-dione, 5-isopropyl-1H-pyrimidinyl-2,4-dione, 5-propynyl-1H-pyrimidinyl-2,4-dione, 5-trifluoromethyl-1H-pyrimidinyl-2,4-dione, 6-amino-9H-purinyl, 2-amino-9H-purinyl, 4-amino-1H-pyrimidinyl-2-one, 4-amino-5-fluoro-1H-pyrimidinyl-2-one, 4-amino-5-methyl-1H-pyrimidinyl-2-one, 2-amino-1,9-dihydro-purinyl-6-one, 1,9-dihydro-purinyl-6-one, 1H-[1,2,4] triazolyl-3-carboxylic acid amide, 2,6-diamino-N.sub.6-cyclopropyl-9H-purinyl, 2-amino-6-(4-methoxyphenylsulfanyl)-9H-purinyl, 5,6-dichloro-1H-benzoimidazolyl, 2-isopropylamino-5,6-dichloro-1H-benzoimidazolyl, 2-bromo-5,6-dichloro-1H-benzoimidazolyl, and the like. Furthermore, the term "saturated heterocyclic" represents an unsubstituted, mono-, di- or trisubstituted monocyclic, polycyclic saturated heterocyclic group covalently attached at any ring position capable of forming a stable covalent bond, certain preferred points of attachment being apparent to those skilled in the art (e.g., 1-piperidinyl, 4-piperazinyl and the like).

Hetero-containing groups may also be substituted. For example, "substituted heterocyclic" refers to a ring-containing group having in the range of 3 up to 14 carbon atoms that contains one or more heteroatoms and also bears one or more substituents, as set forth above. Examples of substituents include, but are not limited to halo, —OH, —SH, —CN, —NO$_2$, trihalomethyl, hydroxypyronyl, $C_{1-10}$alkyl, aryl$C_{1-10}$alkyl, $C_{1-10}$alkyloxy$C_{1-10}$alkyl, aryl$C_{1-10}$alkyloxy $C_{1-10}$alkyl, $C_{1-10}$alkylthio$C_{1-10}$alkyl, aryl$C_{1-10}$alkylthio$C_{1-10}$alkyl, $C_{1-10}$alkylamino$C_{1-10}$alkyl, aryl$C_{1-10}$alkylamino $C_{1-10}$alkyl, N-aryl-N—$C_{1-10}$alkylamino$C_{1-10}$alkyl, $C_{1-10}$alkylcarbonyl$C_{1-10}$alkyl, aryl$C_{1-10}$alkylcarbonyl $C_{1-10}$alkyl, $C_{1-10}$alkylcarboxy$C_{1-10}$alkyl, aryl$C_{1-10}$alkylcarboxy$C_{1-10}$alkyl $C_{1-10}$alkylcarbonylamino$C_{1-10}$alkyl, and aryl$C_{1-10}$alkylcarbonylamino $C_{1-10}$alkyl.

As used herein, the term "phenol" includes compounds having one or more phenolic functions per molecule. The terms aliphatic, cycloaliphatic and aromatic, when used to describe phenols, refers to phenols to which aliphatic, cycloaliphatic and aromatic residues or combinations of these backbones are attached by direct bonding or ring fusion.

As used herein, "alkenyl," "alkene" or "olefin" refers to straight or branched chain unsaturated hydrocarbyl groups having at least one carbon-carbon double bond, and having in the range of about 2 up to 500 carbon atoms. In certain embodiments, alkenyl groups have in the range of about 5 up to about 250 carbon atoms, 5 up to about 100 carbon atoms, 5 up to about 50 carbon atoms or 5 up to about 25 carbon atoms.

In other embodiments, alkenyl groups have in the range of about 6 up to about 500 carbon atoms, 8 up to about 500 carbon atoms, 10 up to about 500 carbon atoms or 20 up to about 500 carbon atoms or 50 up to about 500 carbon atoms. In yet further embodiments, alkenyl groups have in the range of about 6 up to about 100 carbon atoms, 10 up to about 100 carbon atoms, 20 up to about 100 carbon atoms or 50 up to about 100 carbon atoms, while in other embodiments, alkenyl groups have in the range of about 6 up to about 50 carbon atoms, 6 up to about 25 carbon atoms, 10 up to about 50 carbon atoms, or 10 up to about 25 carbon atoms. "Substituted alkenyl" refers to alkenyl groups further bearing one or more substituents as set forth above.

As used herein, "alkylene" refers to a divalent alkyl moiety, and "oxyalkylene" refers to an alkylene moiety containing at least one oxygen atom instead of a methylene (CH$_2$) unit. "Substituted alkylene" and "substituted oxyalkylene" refer to alkylene and oxyalkylene groups further bearing one or more substituents as set forth above.

As used herein, "alkynyl" refers to straight or branched chain hydrocarbyl groups having at least one carbon-carbon triple bond, and having in the range of 2 up to about 100 carbon atoms, typically about 4 to about 50 carbon atoms, and frequently about 8 to about 25 carbon atoms. "Substituted alkynyl" refers to alkynyl groups further bearing one or more substituents as set forth below.

As used herein, "oxiranylene" refers to divalent moieties having the structure:

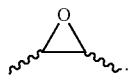

As used herein, "arylene" refers to a divalent aryl moiety. "Substituted arylene" refers to arylene moieties bearing one or more substituents as set forth above.

As used herein, "acyl" refers to alkyl-carbonyl species.

"Allyl" as used herein, refers to refers to a compound bearing at least one moiety having the structure:

"Imide" as used herein, refers to a functional group having two carbonyl groups bound to a primary amine or ammonia. The general formula of an imide of the invention is:

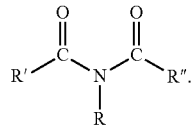

"Polyimides" are polymers of imide-containing monomers. Polyimides are typically linear or cyclic. Non-limiting examples of linear and cyclic (e.g. an aromatic heterocyclic polyimide) polyimides are shown below for illustrative purposes.

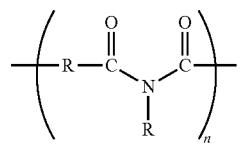
Linear Polyimide

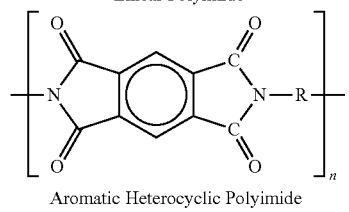
Aromatic Heterocyclic Polyimide

"Maleimide," as used herein, refers to an N-substituted maleimide having the formula as shown below:

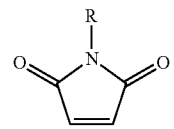

where R is an aromatic, heteroaromatic, aliphatic, or polymeric moiety.

"Bismaleimide" or "BMI", as used herein, refers to compound in which two imide moieties are linked by a bridge, i.e. a compound a polyimide having the general structure shown below:

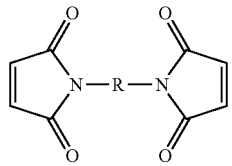

where R is an aromatic, heteroaromatic, aliphatic, or polymeric moiety.

BMIs can cure through an addition rather than a condensation reaction, thus avoiding problems resulting from the formation of volatiles. BMIs can be cured by a vinyl-type polymerization of a pre-polymer terminated with two maleimide groups.

As used herein, the term "acrylate" refers to a compound bearing at least one moiety having the structure:

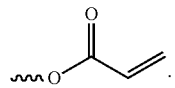

As used herein, the term "acrylamide" refers to a compound bearing at least one moiety having the structure:

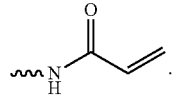

As used herein, the term "methacrylate" refers to a compound bearing at least one moiety having the structure:

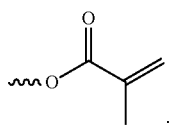

As used herein, the term "methacrylamide" refers to a compound bearing at least one moiety having the structure:

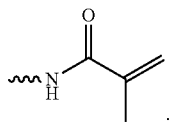

As used herein, "maleate" refers to a compound bearing at least one moiety having the structure:

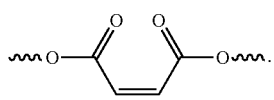

As used herein, the term "acyloxy benzoate" or "phenyl ester" refers to a compound bearing at least one moiety having the structure:

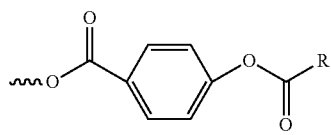

wherein R=H, lower alkyl, or aryl.

As used herein, the term "citraconimide" refers to a compound bearing at least one moiety having the structure:

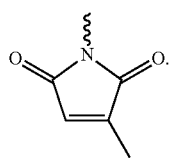

"Itaconate", as used herein refers to a compound bearing at least one moiety having the structure:

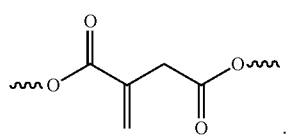

As used herein, the terms "halogen," "halide," or "halo" include fluorine, chlorine, bromine, and iodine.

As used herein, "siloxane" refers to any compound containing a Si—O moiety. Siloxanes may be either linear or cyclic. In certain embodiments, siloxanes of the invention include 2 or more repeating units of Si—O. Exemplary cyclic siloxanes include hexamethylcyclotrisiloxane, octamethylcyclotetrasiloxane, decamethylcyclopentasiloxane, dodecamethylcyclohexasiloxane and the like.

As used herein, "oxiranylene" or "epoxy" refers to divalent moieties having the structure:

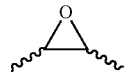

The term "epoxy" also refers to thermosetting epoxide polymers that cure by polymerization and crosslinking when mixed with a catalyzing agent or "hardener," also referred to as a "curing agent" or "curative." Epoxies of the present invention include, but are not limited to aliphatic, cycloaliphatic, glycidyl ether, glycidyl ester, glycidyl amine epoxies, and the like, and combinations thereof.

As used herein, the term "oxetane" refers to a compound bearing at least one moiety having the structure:

As used herein, the term "vinyl ether" refers to a compound bearing at least one moiety having the structure:

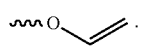

As used herein, the term "vinyl ester" refers to a compound bearing at least one moiety having the structure:

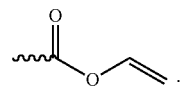

As used herein, "styrenic" refers to a compound bearing at least one moiety having the structure:

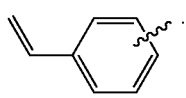

"Oxazoline" as used herein, refers to a compound bearing at least one moiety having the structure:

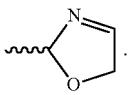

"Benzoxazine" as used herein, refers to a compound bearing at least one moiety having the structure:

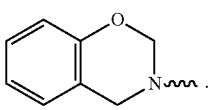

"Fumarate" as used herein, refers to a compound bearing at least one moiety having the structure:

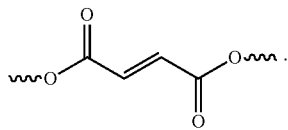

"Propargyl" as used herein, refers to a compound bearing at least one moiety having the structure:

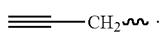

"Cyanate" as used herein, refers to a compound bearing at least one moiety having the structure:

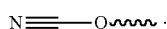

As used herein, "norbornyl" refers to a compound bearing at least one moiety having the structure:

As used herein, a "primary amine terminated difunctional siloxane bridging group" refers to a moiety having the structural formula:

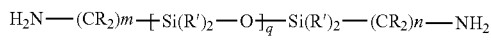

where each R is H or Me, each R' is independently H, lower alkyl, or aryl; each of m and n is an integer having the value between 1 to about 10, and q is an integer having the value between 1 and 100.

As used herein a "primary amine terminated polypropylene oxide" refers to a moiety having the structural formula:

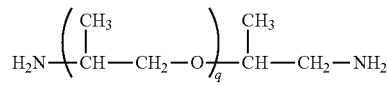

where q is 4 to about 50.

As used herein a "primary amine terminated butadiene acrylonitrile copolymer" refers to a moiety having the structural formula:

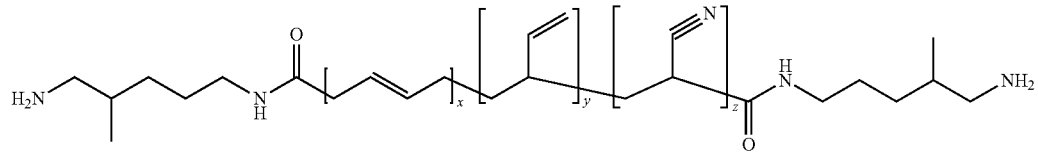

where each x and y are independently 0 to about 20; x plus y is about 10 to about 20, and z is about 1 to 5.

As used herein, the term "free radical initiator" refers to any chemical species which, upon exposure to sufficient energy (e.g., light, heat, or the like), decomposes into parts which are uncharged, but every one of such part possesses at least one unpaired electron.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

"Diamine," as used herein, refers generally to a compound or mixture of compounds, where each species has 2 amine groups.

A "diol" according to the present invention, is a compound containing two hydroxyl groups (—OH groups); while "polyol" refers to alcohols containing multiple hydroxyl groups.

The term "solvent," as used herein, refers to a liquid that dissolves a solid, liquid, or gaseous solute, resulting in a solution. "Co-solvent" refers to a second, third, etc. solvent used with a primary solvent.

As used herein, "polar protic solvents" are ones that contain an O—H or N—H bond, while "polar aprotic solvents" do not contain an O—H or N—H bond.

As used herein, "alcohol catalyst" refers to an alcohol or combination of alcohols that, when added to a chemical reaction, has the effect of accelerating, increasing the rate or yield of the reaction without being consumed by the overall reaction. Typically, an alcohol catalyst will contain a single alcohol, but mixtures comprising two or more alcohols are contemplated for use in the present invention. As used herein, "acid catalyst" refers to any acidic substance or compound that, when added to a chemical reaction, has the effect of accelerating, increasing the rate or yield of the reaction without being consumed by the overall reaction. Typically, an acid catalyst will contain a single acid, but mixtures comprising two or more acids are contemplated for use in the present invention. Acid catalysts of the invention can be soluble or insoluble. For example, polymer-bound acid catalysts may conveniently be used in the methods of the invention and then easily removed e.g. by gravity filtration.

The "Michael reaction" or "Michael addition" is the nucleophilic addition of a carbanion to an alpha, beta unsaturated carbonyl compound. It belongs to the larger class of conjugate additions and is one of the most useful methods for mild formation of C—C bonds. The general scheme for Michael addition reactions is shown below Michael Addition Reaction Scheme

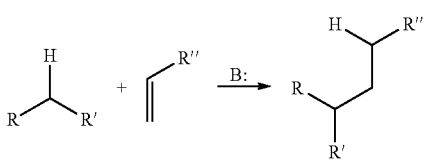

In this scheme the R and R' substituents on the nucleophile ("Michael donor") are electron-withdrawing groups such as acyl and cyano making the methylene hydrogen acidic forming the carbanion on reaction with base B:. The substituent on the activated alkene ("Michael acceptor") is usually a ketone making it an enone, but can also be a nitro group.

"Friedel-Crafts alkylation" is an electrophilic aromatic substitution that involves the alkylation of an aromatic ring with an alkyl halide using a strong Lewis acid catalyst. A typical reaction scheme for alkylation of a benzene ring is shown below:

Friedel Crafts Alkylation Scheme

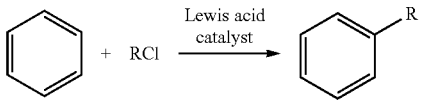

"Prilezhaev reaction" is a method for synthesizing epoxy compounds are by reacting olefins with peroxides; the later provide an oxygen atom that becomes a part of the resulting epoxy compound. Some peroxide reagents that may be used include hydrogen peroxide, peroxycarboxylic acids, and alkyl hydroperoxides. The Prilezhaev reaction may be schematically illustrated by the following reaction scheme demonstrating the formation of an epoxy compound from styrene:

Prilezhaev Reaction Scheme

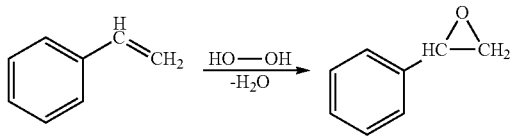

"Glass transition temperature" or "$T_g$": is used herein to refer to the temperature at which an amorphous solid, such as a polymer, becomes brittle on cooling, or soft on heating. More specifically, it defines a pseudo second order phase transition in which a supercooled melt yields, on cooling, a glassy structure and properties similar to those of crystalline materials e.g. of an isotropic solid material.

"Modulus" or "Young's modulus" as used herein, is a measure of the stiffness of a material. Within the limits of elasticity, modulus is the ratio of the linear stress to the linear strain which can be determined from the slope of a stress-strain curve created during tensile testing.

The "Coefficient of Thermal Expansion" or "CTE" is a term of art describing a thermodynamic property of a substance. The CTE relates a change in temperature to the change in a material's linear dimensions. As used herein "$\alpha_1$ CTE" or "$\alpha_1$" refers to the CTE before the $T_g$, while "$\alpha_2$ CTE" refers to the CTE after the $T_g$.

"Thixotropy" as used herein, refers to the property of a material which enables it to stiffen or thicken in a relatively short time upon standing, but upon agitation or manipulation to change to low-viscosity fluid; the longer the fluid undergoes shear stress, the lower its viscosity. Thixotropic materials are therefore gel-like at rest but fluid when agitated and have high static shear strength and low dynamic shear strength, at the same time.

"Thermogravimetric analysis" or "TGA" refers to a method of testing and analyzing a material to determine changes in weight of a sample that is being heated in relation to change in temperature. "Decomposition onset" refers to a temperature when the loss of weight in response to the increase of the temperature indicates that the sample is beginning to degrade.

In certain embodiments, R and Q are each independently substituted or unsubstituted linear, branched, or cyclic aliphatic or alkenyl moieties having from 2 to about 500 carbon atoms. In other embodiments, R and Q are each independently substituted or unsubstituted aromatic or heteroaromatic moieties having from 6 to about 20 carbon atoms.

In other embodiments, R and Q are each independently substituted or unsubstituted siloxane moieties having from 2 to about 1000 silicon atoms. In some embodiments, R and Q are each independently polysiloxane moieties, such as, for example, dimethylsiloxane, methylphenylsiloxane, diphenylsiloxane, methylhydrosiloxane, or combinations thereof.

When R and Q include substituted aliphatic, aromatic, heteroaromatic, or siloxane moieties, such substituents include alkyl, alkenyl, alkynyl, hydroxy, oxo, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, haloalkyl, cyano, nitro, nitrone, amino, amido, —C(O)H, —C(O)—, —S—, —S(O)2—, —OC(O)—O—, —NR—C(O)—, —NR—C(O)—NR—, —OC(O)—NR—, wherein R is H or lower alkyl, acyl, oxyacyl, carboxyl, carbamate, sulfonyl, sulfonamide, sulfuryl, and the like.

In another embodiment, there are provided compounds having the structure:

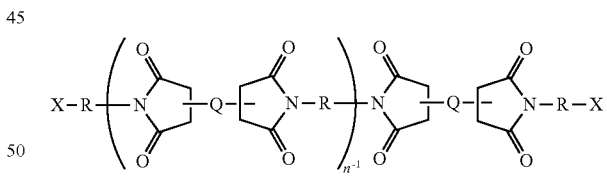

where R and Q are each independently substituted or unsubstituted aliphatic, aromatic, heteroaromatic, siloxane, unsaturated hydrocarbon, polyester, polyamide, or polyurethane moieties; and X is a polymerizable or curative moiety.

In some embodiments, the polymerizable moiety is a cationic polymerizable moiety, an anionic polymerizable moiety, a ring-opening polymerizable moiety, or a free radical polymerizable moiety. In some embodiments, the polymerizable moiety is vinyl ether, vinyl ester, acrylate, methacrylate, epoxy, oxetane, oxazoline, benzoxazine, prorpargyl ether, urethane, norbornyl, maleimide, or nadimide. In some embodiments the curative is phenol, phenyl ester and the like.

Referring to FIG. 1, imide-extended bismaleimide compounds are readily prepared by a two-step, single-pot synthesis. The first step involves the condensation of a dianhydride with a dimer diamine to form an amine-terminated polyimide. The diamine should be present in at least a slight excess of that necessary to form the imide-linked diamine intermediate.

A wide variety of diamines are contemplated for use in the practice of the invention, such as for example, 1,10-diaminodecane; 1,12-diaminododecane; dimer diamine; 1,2-diamino-2-methylpropane; 1,2-diaminocyclohexane; 1,2-diaminopropane; 1,3-diaminopropane; 1,4-diaminobutane; 1,5-diaminopentane; 1,7-diaminoheptane; 1,8-diaminomenthane; 1,8-diaminooctane; 1,9-diaminononane; 3,3'-diamino-N-methyldipropylamine; diaminomaleonitrile; 1,3-diaminopentane; 9,10-diaminophenanthrene; 4,4'-diaminooctafluorobiphenyl; 3,5-diaminobenzoic acid; 3,7-diamino-2-methoxyfluorene; 4,4'-diaminobenzophenone; 3,4-diaminobenzophenone; 3,4-diaminotoluene; 2,6-diaminoanthroquinone; 2,6-diaminotoluene; 2,3-diaminotoluene; 1,8-diaminonaphthalene; 2,4-diaminotoluene; 2,5-diaminotoluene; 1,4-diaminoanthroquinone; 1,5-diaminoanthroquinone; 1,5-diaminonaphthalene; 1,2-diaminoanthroquinone; 2,4-cumenediamine; 1,3-bisaminomethylbenzene; 1,3-bisaminomethylcyclohexane; 2-chloro-1,4-diaminobenzene; 1,4-diamino-2,5-dichlorobenzne; 1,4-diamino-2,5-dimethylbenzene; 4,4'-diamino-2,2'-bistrifluoromethylbiphenyl; bis(amino-3-chlorophenyl)ethane; bis(4-amino-3,5-dimethylphenyl)methane; bis(4-amino-3,5-diethylphenyl) methane; bis(4-amino-3-ethyl diaminofluorene; diaminobenzoic acid; 2,3-diaminonaphthalene; 2,3-diaminophenol; -5-methylphenyl)methane; bis(4-amino-3-methylphenyl)methane; bis(4-amino-3-ethylphenyl)methane; 4,4'-diaminophenylsulfone; 3,3'-diaminophenylsulfone; 2,2-bis(4,-(4-aminophenoxy)phenyl)sulfone; 2,2-bis(4-(3-aminophenoxy)phenyl)sulfone; 4,4'-oxydianiline; 4,4'-diaminodiphenyl sulfide; 3,4'-oxydianiline; 2,2-bis(4-(4-aminophenoxy)phenyl)propane; 1,3-bis(4-aminophenoxy) benzene; 4,4'-bis(4-aminophenoxy)biphenyl; 4,4'-diamino-3,3'-dihydroxybiphenyl; 4,4'-diamino-3,3'-dimethylbiphenyl; 4,4'-diamino-3,3'-dimethoxybiphenyl; Bisaniline M; Bisaniline P; 9,9-bis(4-aminophenyl)fluorene; o-tolidine sulfone; methylene bis(anthranilic acid); 1,3-bis(4-aminophenoxy)-2,2-dimethylpropane; 1,3-bis(4-aminophenoxy)propane; 1,4-bis(4-aminophenoxy)butane; 1,5-bis(4-aminophenoxy)butane; 2,3,5,6-tetramethyl-1,4-phenylenediamine; 3,3',5,5'-tetramehylbenzidine; 4,4'-diaminobenzanilide; 2,2-bis(4-aminophenyl) hexafluoropropane; polyoxyalkylenediamines (e.g. Huntsman's Jeffamine D-230, D400, D-2000, and D-4000 products); 1,3-cyclohexanebis(methylamine); m-xylylenediamine; p-xylylenediamine; bis(4-amino-3-methylcyclohexyl)methane; 1,2-bis(2-aminoethoxy)ethane; 3(4),8(9)-bis (aminomethyl)tricyclo(5.2.1.0$^{2,6}$)decane; and the like.

The second step of the reaction involves the condensation of the remaining amine residues with a slight excess of maleic anhydride to form the maleimide moieties. This second step can be accomplished employing techniques well known to those of skill in the art. The most straightforward preparation of maleimides entails formation of the maleamic acid via reaction of the primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amines, may require forcing conditions which can lower the yield. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-hydroxybenzotriazole (HOBt), the product is solely the maleimide. The function of the HOBt could be to allow the closure to proceed via the HOBt ester of the maleamic acid (formed via the agency of DCC) which presumably closes preferentially to the maleimide. Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent. An alternative method for affecting the cyclodehydration of maleamic acids is set forth in U.S. Pat. No. 5,973,166, the entire contents of which are incorporated herein by reference. This method utilizes amine salts that can be successfully used to replace the polar, aprotic solvents that have been used for the cyclodehydration of maleamic acids. The use of these salts provides competitive reaction times and product yields relative to results obtained with polar, aprotic solvents. These salts have the advantage of having no vapor pressure and, therefore, have no possibility to co-distill with the water produced by the cyclodehydration reaction. Furthermore, such salts can be tailored to have desirable solubility characteristics (i.e., soluble in the refluxing azeotropic solvent, but insoluble at room temperature) that permit their easy removal from the reaction product. Such salts are not destroyed during the cyclodehydration reaction and, therefore, can be efficiently recycled again and again.

A wide variety of anhydrides are contemplated for use in the practice of the invention, such as, for example, polybutadiene-graft-maleic anhydride; polyethylene-graft-maleic anhydride; polyethylene-alt-maleic anhydride; polymaleic anhydride-alt-1-octadecene; polypropylene-graft-maleic anhydride; poly(styrene-co-maleic anhydride); pyromellitic dianhydride; maleic anhydride, succinic anhydride; 1,2,3,4-cyclobutanetetracarboxylic dianhydride; 1,4,5,8-naphthalenetetracarboxylic dianhydride; 3,4,9,10-perylenentetracarboxylic dianhydride; bicyclo(2.2.2)oct-7-ene-2,3,5,6-tetracarboxylic dianhydride; diethylenetriaminepentaacetic dianhydride; ethylenediaminetetraacetic dianhydride; 3,3',4, 4'-benzophenone tetracarboxylic dianhydride; 3,3',4,4'-biphenyl tetracarboxylic dianhydride; 4,4'-oxydiphthalic anhydride; 3,3',4,4'-diphenylsulfone tetracarboxylic dianhydride; 2,2'-bis(3,4-dicarboxyphenyl)hexafluoropropane dianhydride; 4,4'-bisphenol A diphthalic anhydride; 5-(2,5-dioxytetrahydro)-3-methyl-3-cyclohexene-1,2-dicarboxylic anhydride; ethylene glycol bis(trimellitic anhydride); hydroquinone diphthalic anhydride; allyl nadic anhydride; 2-octen-1-ylsuccinic anhydride; phthalic anhydride; 1,2,3,6-tetrahydrophthalic anhydride; 3,4,5,6-tetrahydrophthalic anhydride; 1,8-naphthalic anhydride; glutaric anhydride; dodecenylsuccinic anhydride; hexadecenylsuccinic anhydride; hexahydrophthalic anhydride; methylhexahydrophthalic anhydride; tetradecenylsuccinic anhydride; and the like.

Additional anhydrides contemplated for use include, but are not limited to:
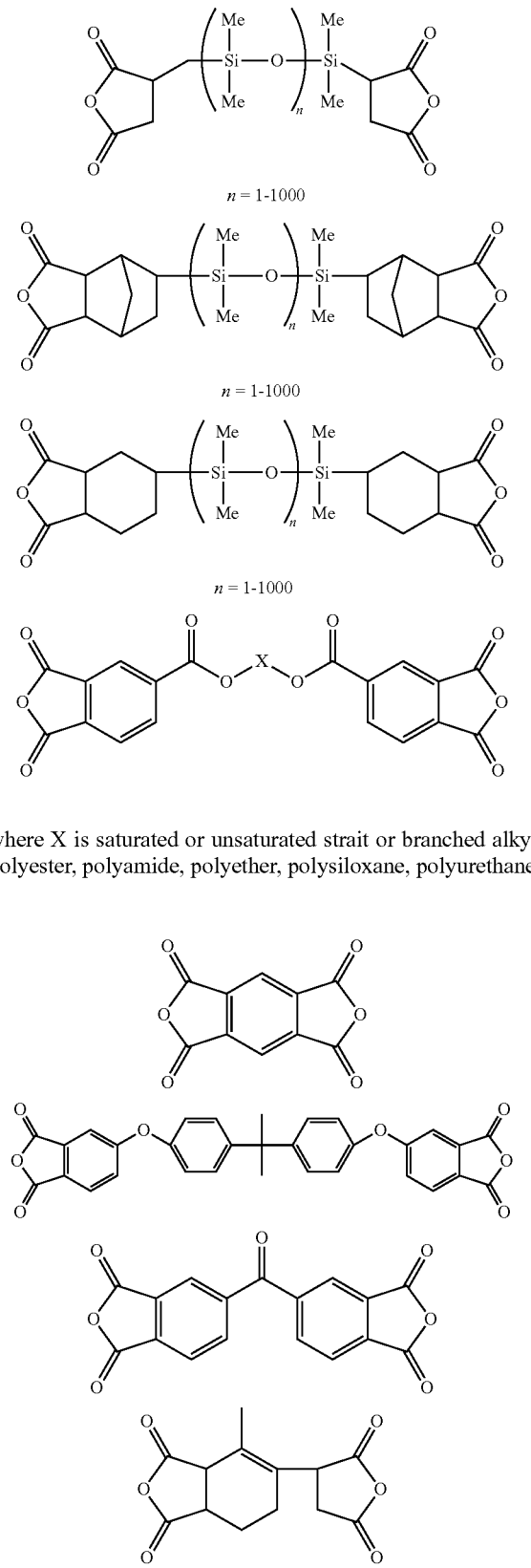
where X is saturated or unsaturated strait or branched alkyl polyester, polyamide, polyether, polysiloxane, polyurethane
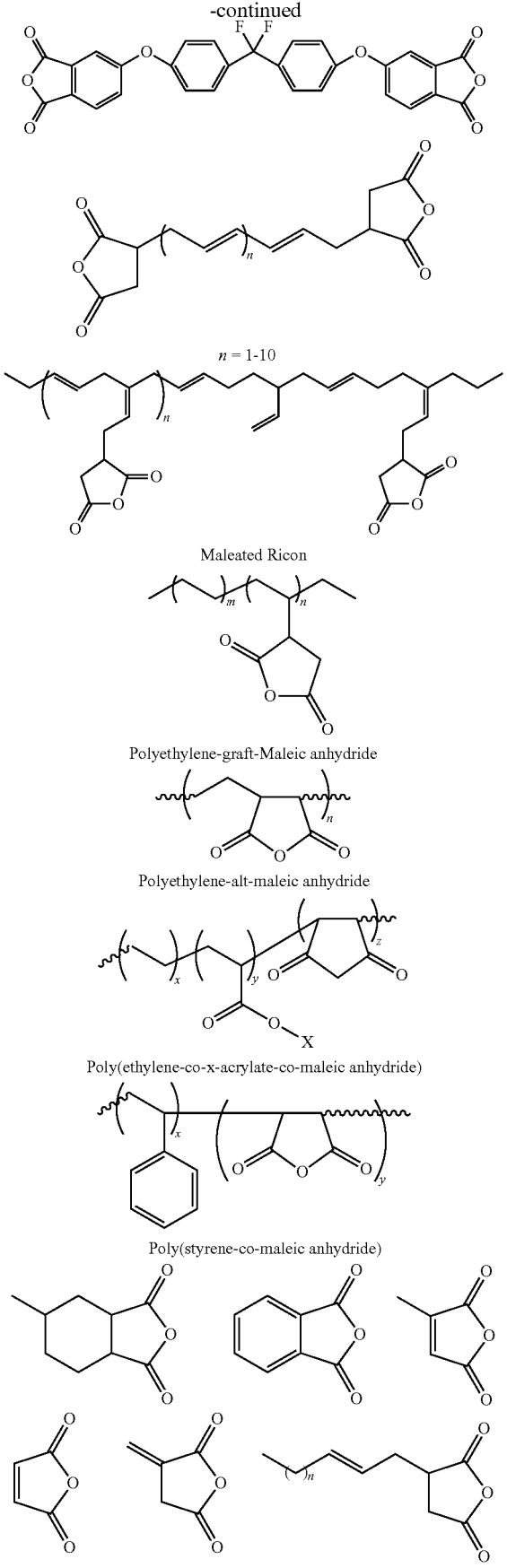

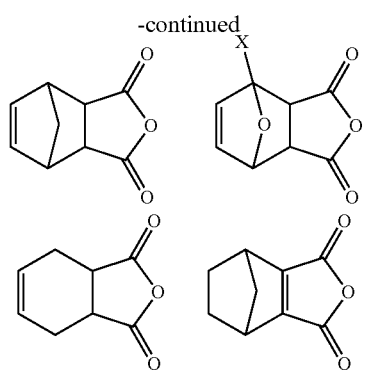
All of the following compounds are also contemplated for use in the practice of the invention:
Maleimides, Citraconimides, and Itaconimides
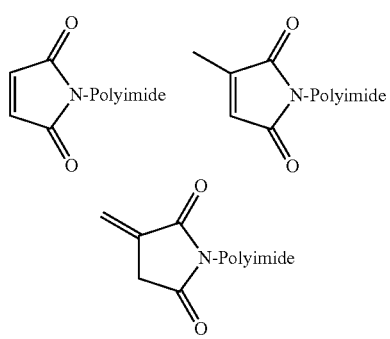
Other Alkene End Groups
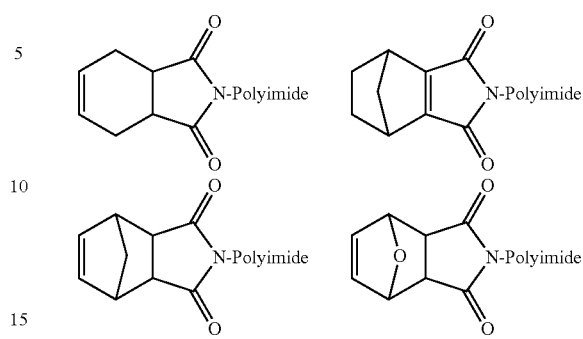
Cycloaliphatic Epoxies
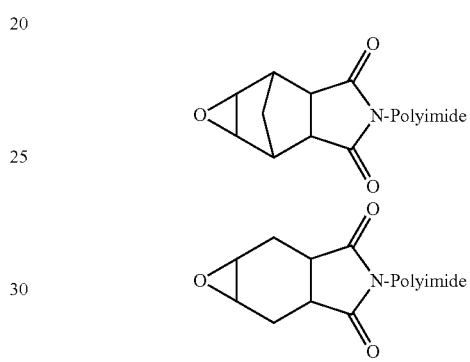
Amines, Alcohols, Carboxylic Acids, Phenols, Thiols.
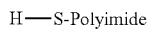   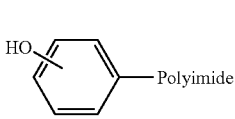 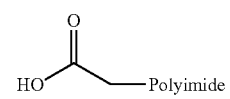
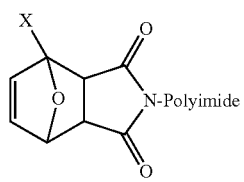 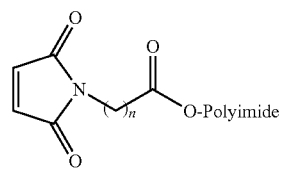 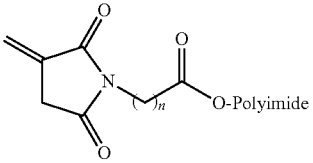
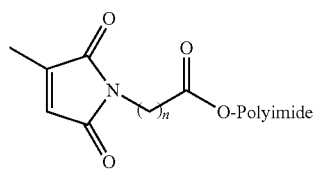 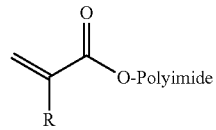 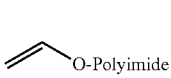 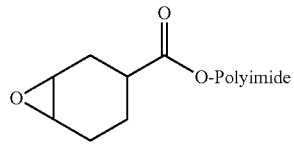
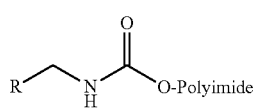 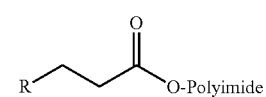 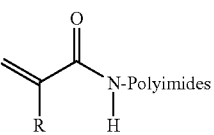 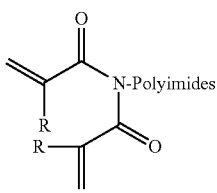

-continued
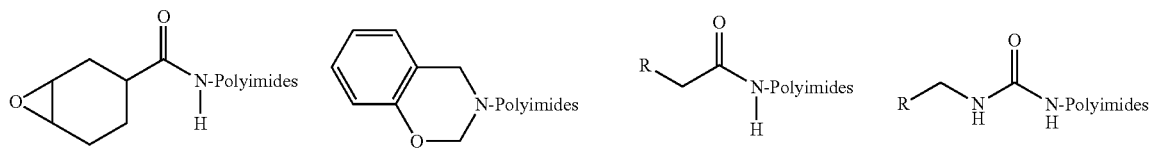
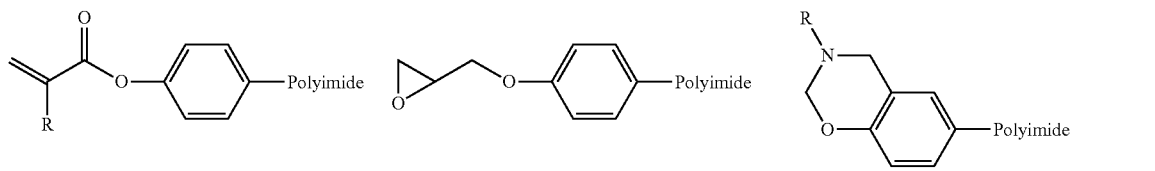
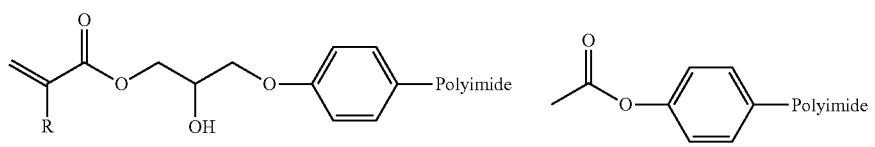
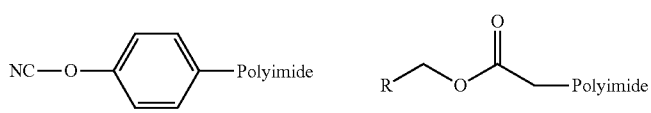
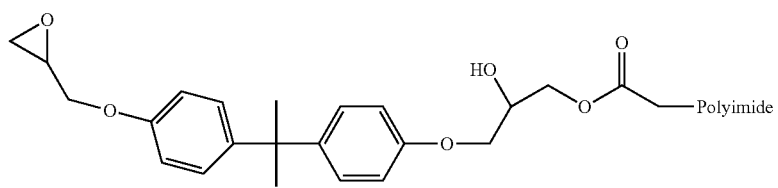
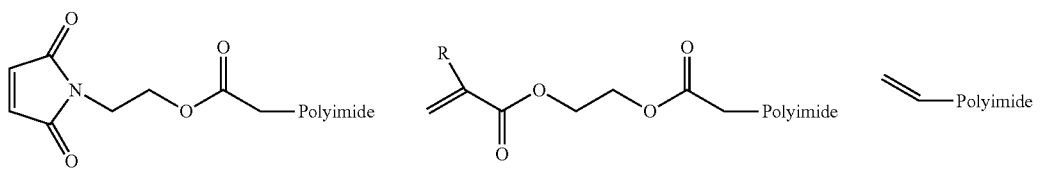
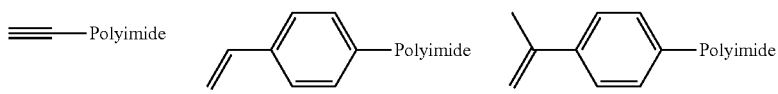
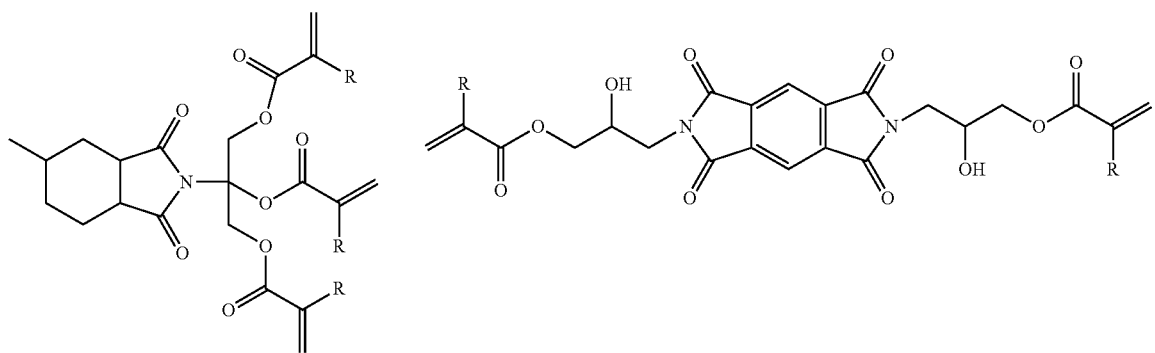

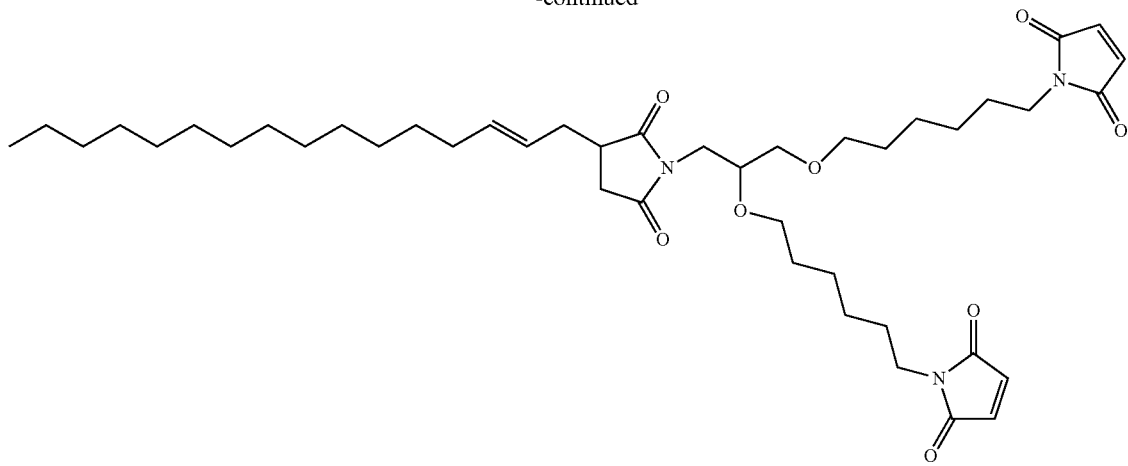

As set forth in the Examples herein, imide-extended maleimide compounds remain flexible at room temperature and are tougher than currently available maleimide-terminated rubbers. Thus, they may be used alone in adhesive compositions or added to available resins as a toughening agent. The maleimides of the invention will be present in the curable adhesive compositions in an amount from 0.05 to 98 weight percent (wt %) based on the organic components present (excluding any fillers).

In another embodiment, there are provided monomaleimides having the formula:

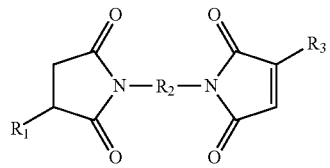

wherein $R_1$ is a substituted or an unsubstituted aliphatic, alkenyl, or aromatic moiety; and $R_2$ is a substituted or an unsubstituted aliphatic, alkenyl, aromatic, or siloxane moiety; and $R_3$ is H or methyl.

In some embodiments, each of $R_1$ and $R_2$ is independently a substituted or an unsubstituted linear, branched, or cyclic aliphatic or alkenyl moieties having from 2 to about 500 carbon atoms. In other embodiments, $R_1$ is a substituted or an unsubstituted aromatic or heteroaromatic moiety having from 6 to about 14 carbon atoms.

In certain other embodiments, $R_2$ is a substituted or an unsubstituted siloxane moiety having from 2 to about 1000 silicon atoms. In some embodiments, $R_2$ is a polysiloxane moiety, such as, for example, dimethylsiloxane, methylphenylsiloxane, diphenylsiloxane, or combinations thereof.

When $R_1$ and $R_2$ are substituted, the substituents present are those as set forth above.

In another embodiment of the invention, there are provided polymaleimides including polymers having a plurality of pendant repeating units having the structure:

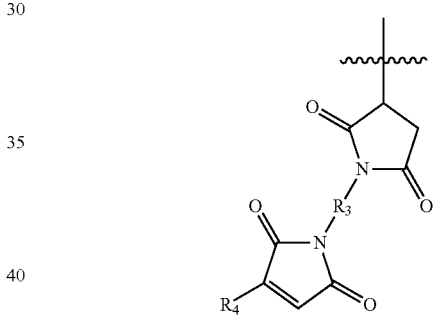

wherein $R_3$ is a substituted or an unsubstituted aliphatic, alkenyl, aromatic, heteroaromatic, or siloxane moiety; and $R_4$ is H or methyl As used herein, the term "pendant" means that the structure set forth above is attached to a polymer main chain through at least one covalent bond.

In some embodiments, $R_3$ is a substituted or an unsubstituted linear, branched, or cyclic aliphatic or alkenyl moiety having from 2 to about 500 carbon atoms. In other embodiments, $R_3$ is a substituted or an unsubstituted aromatic or heteroaromatic moiety having from 6 to about 14 carbon atoms. In other embodiments, $R_3$ is a substituted or an unsubstituted siloxane moiety having from 2 to about 1000 silicon atoms. $R_3$ can also be a polysiloxane, such as, for example, dimethylsiloxane, methylphenylsiloxane, diphenylsiloxane, or combinations thereof. When $R_3$ is substituted, the substituents are as set forth above.

In a further embodiment, there are provided polymaleimide polymers including a plurality of repeating units having the structure:

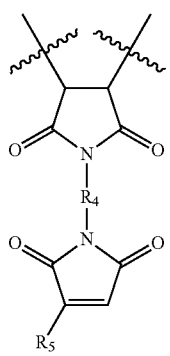

wherein $R_4$ is a substituted or an unsubstituted linear, branched, or cyclic aliphatic or alkenyl moiety having from 2 to about 500 carbon atoms, or an aromatic moiety; and $R_5$ is H or methyl.

In some embodiments, $R_4$ is a substituted or an unsubstituted linear, branched, or cyclic aliphatic or alkenyl moiety having from 2 to about 500 carbon atoms. In other embodiments, $R_4$ is a substituted or an unsubstituted aromatic or heteroaromatic moiety having from 6 to about 14 carbon atoms. In other embodiments, $R_4$ is a substituted or an unsubstituted siloxane moiety having from 2 to about 1000 silicon atoms. $R_4$ can also be a polysiloxane, such as, for example, dimethylsiloxane, methylphenylsiloxane, diphenylsiloxane, methylhydrosiloxane, or combinations thereof. When $R_4$ is substituted, the substituents are as set forth above.

Figure 3:
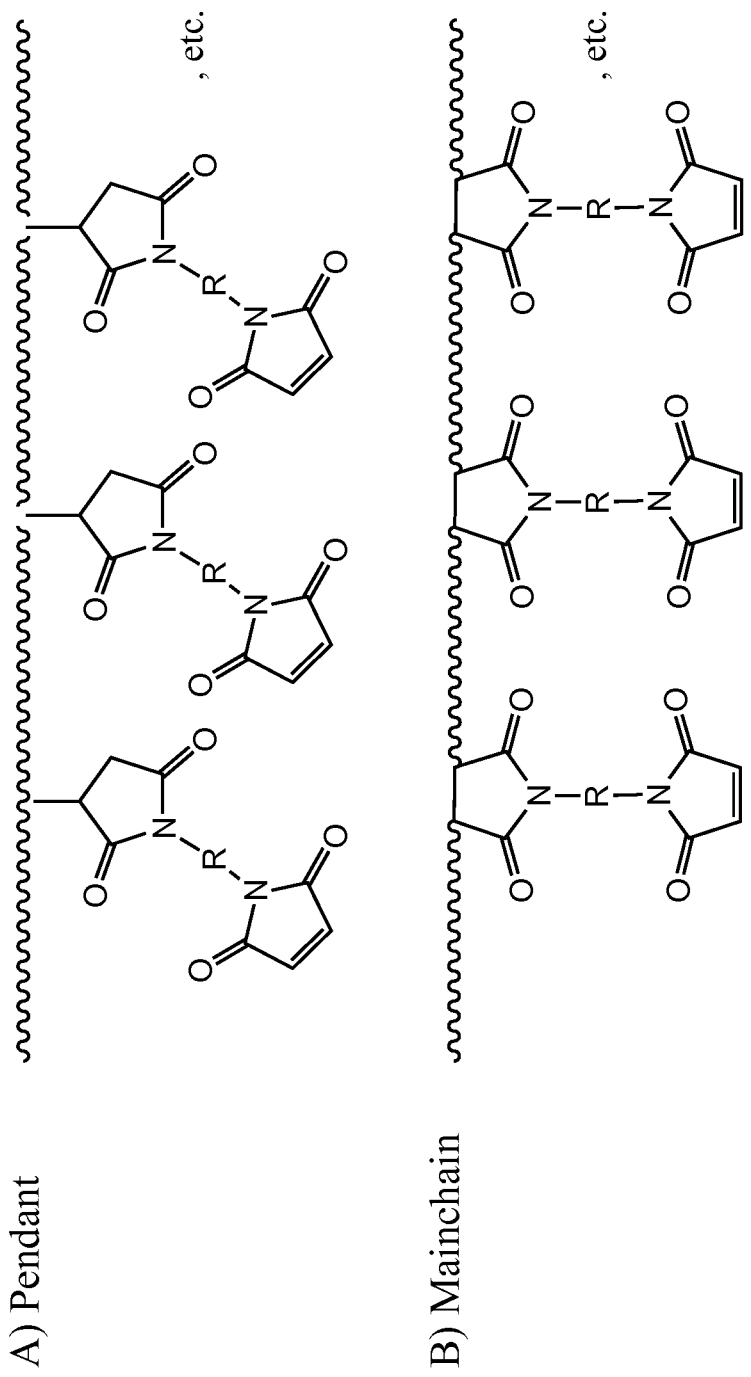
FIG. 3 shows the generic structure of exemplary polymaleimides of the invention.

Examples of such polymaleimides are shown in FIG. 3. The precursor polymers or oligomers with pendant or main-chain succinic anhydride functional groups are known in the art. Examples of such materials include polyolefins (e.g., polyethylene, polypropylene, and the like) grafted with succinic anhydride residues, polybutadiene grafted with succinic anhydride residues, alternating or random copolymers of maleic anhydride with styrene or -olefins, and the like. In order to prepare the polymaleimides of the invention, a large excess of diamine is typically used in order to suppress undesirable cross-linking reactions.

The imide-extended mono-, bis, and polymaleimides of the invention may be used independently in adhesive compositions, or may be combined with other adhesive compounds and resins. In one embodiment, the bismaleimide monomer of the invention may be used as the sole thermoset monomer of the adhesive composition. In another embodiment, the bismaleimide monomer of the invention may be with other thermoset monomers to make a fully formulated adhesive.

In one embodiment, there is provided an adhesive composition including an imide-extended bismaleimide compound and at least one curing initiator.

In some embodiments, the imide-extended bismaleimide compound is present in the composition from 0.05 weight percent to about 98 weight percent (wt %) based on total weight of the composition. In other embodiments, there is at least one co-monomer typically is present in the composition from 10 wt % to about 90 wt % based on total weight of the composition. Such comonomers include, for example, acrylates, methacrylates, maleimides, vinyl ethers, vinyl esters, styrenic compounds, allyl functional compounds, epoxy, oxetane, phenols, phenyl esters, and the like.

The at least one curing initiator is typically present in the composition from 0.1 wt % to about 5 wt % based on total weight of the composition, and is typically a free-radical initiator. As used herein, the term "free radical initiator" refers to any chemical species which, upon exposure to sufficient energy (e.g., light, heat, or the like), decomposes into two parts which are uncharged, but which each possess at least one unpaired electron. Some free radical initiators contemplated for use in the practice of the present invention are compounds which decompose (i.e., have a half life in the range of about 10 hours) at temperatures in the range of about 70° C. up to 180° C. Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methylpropanenitrile), 2,2'-azobis(2-methylbutanenitrile), and 1,1'-azobis(cyclohexanecarbonitrile)), and the like.

The term "free radical initiator" also includes photoinitiators. For example, for invention adhesive compositions that contain a photoinitiator, the curing process can be initiated by UV radiation. In one embodiment, the photoinitiator is present at a concentration of 0.1 wt % to 5 wt % based on the total weight of the organic compounds in the composition (excluding any filler). In a one embodiment, the photoinitiator comprises 0.1 wt % to 3.0 wt %, based on the total weight of the organic compounds in the composition. Photoinitiators include benzoin derivatives, benzilketals, α,α-dialkoxyacetophenones, α-hydroxyalkylphenones, α-aminoalkylphenones, acylphosphine oxides, titanocene compounds, combinations of benzophenones and amines or Michler's ketone, and the like.

In another embodiment of the invention, there are provided die-attach pastes including 0.05 weight percent to about 98 weight percent (wt %) of at least one imide-extended mono-, bis-, or polymaleimide compound described herein, or combinations thereof, based on total weight of the composition; optionally, 10 wt % to about 90 wt % of at least one co-monomer selected from the group consisting of acrylates, methacrylates, maleimides, vinyl ethers, vinyl esters, styrenic compounds, and allyl functional compounds, epoxies, oxetanes, phenols, phenyl esters, and the like, based on total weight of the composition; 0 to about 90 wt % of a filler; 0.1 wt % to about 5 wt % of at least one curing initiator, based on total weight of the composition; and 0.1 wt % to about 4 wt %, of at least one coupling agent, based on total weight of the composition.

In one embodiment, there is provided die-attach paste comprising:

a) 0.05 weight percent to about 98 weight percent (wt %) based on total weight of the composition, an imide-extended bismaleimide having the structure:

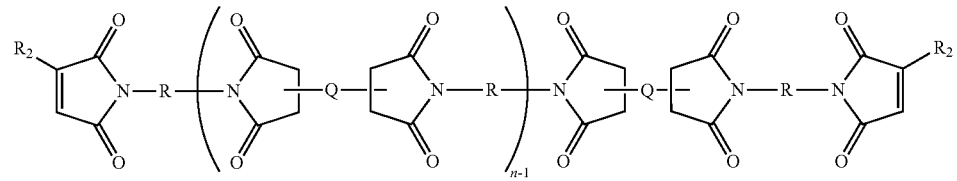

wherein each of R and Q is independently a substituted or an unsubstituted aliphatic, alkenyl, aromatic, heteroaromatic, or siloxane moiety; $R_2$ is H or methyl; and n is an integer having the value between 1 and about 10, with the proviso that the imide-extended bismaleimide is not In general, these compositions will cure within a temperature range of 80-360° C., and curing will be effected within a length of time of less than 1 minute to 120 minutes. As will be understood by those skilled in the art, the time and temperature curing profile for each adhesive composition will vary,

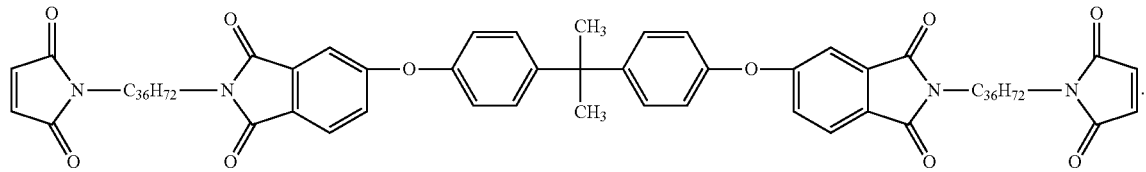

b) 0 to about 90 wt % of a filler;
d) 0.1 wt % to about 5 wt % of at least one curing initiator, based on total weight of the composition;
e) 0.1 wt % to about 4 wt %, of at least one coupling agent, based on total weight of the composition.

Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, copper-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include silica, fumed silica, alumina, titania, and the like.

As used herein, the term "coupling agent" refers to chemical species that are capable of bonding to a mineral surface and which also contain polymerizably reactive functional group(s) so as to enable interaction with the adhesive composition. Coupling agents thus facilitate linkage of the die-attach paste to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), zirconates, or compounds that contain a copolymerizable group and a chelating ligand (e.g., phosphine, mercaptan, acetoacetate, and the like). In some embodiments, the coupling agents contain both a co-polymerizable function (e.g., vinyl moiety, acrylate moiety, methacrylate moiety, and the like), as well as a silicate ester function. The silicate ester portion of the coupling agent is capable of condensing with metal hydroxides present on the mineral surface of substrate, while the co-polymerizable function is capable of co-polymerizing with the other reactive components of invention die-attach paste. In certain embodiments coupling agents contemplated for use in the practice of the invention are oligomeric silicate coupling agents such as poly(methoxyvinylsiloxane).

In some embodiments, both photoinitiation and thermal initiation may be desirable. For example, curing of a photoinitiator-containing adhesive can be started by UV irradiation, and in a later processing step, curing can be completed by the application of heat to accomplish a free-radical cure. Both UV and thermal initiators may therefore be added to the adhesive composition.

and different compositions can be designed to provide the curing profile that will be suited to the particular industrial manufacturing process.

In certain embodiments, the adhesive compositions may contain compounds that lend additional flexibility and toughness to the resultant cured adhesive. Such compounds may be any thermoset or thermoplastic material having a $T_g$ of 50° C. or less, and typically will be a polymeric material characterized by free rotation about the chemical bonds, the presence of ether groups, and the absence of ring structures. Suitable such modifiers include polyacrylates, poly(butadiene), poly-THF (polymerized tetrahydrofuran, also known as poly(1,4-butanediol)), CTBN (carboxy-terminated butadiene-acrylonitrile) rubber, and polypropylene glycol. When present, toughening compounds may be in an amount up to about 15 percent by weight of the maleimide and other monofunctional vinyl compound.

Inhibitors for free-radical cure may also be added to the adhesive compositions and die-attach pastes described herein to extend the useful shelf life of compositions containing the imide-extended maleimides. Examples of these inhibitors include hindered phenols such as 2,6-di-tert-butyl-4-methylphenol; 2,6-di-tert-butyl-4-methoxyphenol; tert-butyl hydroquinone; tetrakis(methylene(3,5-di-tert-butyl-4-hydroxyhydrocinnamate))benzene; 2,2'-methylenebis(6-tert-butyl-p-cresol); and 1,3,5-trimethyl-2,4,6-tris(3',5'-di-tert-butyl-4-hydroxybenzyl)benzene. Other useful hydrogen-donating antioxidants include derivatives of p-phenylenediamine and diphenylamine. It is also well know in the art that hydrogen-donating antioxidants may be synergistically combined with quinones, and metal deactivators to make a very efficient inhibitor package. Examples of suitable quinones include benzoquinone, 2-tert butyl-1,4-benzoquinone; 2-phenyl-1,4-benzoquinone; naphthoquinone, and 2,5-dichloro-1,4-benzoquinone. Examples of metal deactivators include N,N'-bis(3,5-di-tert-butyl-4-hydroxyhydrocinnamoyl)hydrazine; oxalyl bis(benzylidenehydrazide); and N-phenyl-N'-(4-toluenesulfonyl)-p-phenylenediamine. Nitroxyl radical compounds such as TEMPO (2,2,6,6-tetramethyl-1-piperidnyloxy, free radical) are also effective as inhibitors at low concentrations. The total amount of antioxidant plus synergists typically falls in the range of 100 to 2000 ppm relative to the weight of total base resin. Other additives, such as adhesion promoters, in types and amounts known in the art, may also be added.

These compositions will perform within the commercially acceptable range for die attach adhesives. Commercially acceptable values for die shear for the adhesives on a 80×80 $mil^2$ silicon die are in the range of greater than or equal to 1 kg at room temperature, and greater than or equal to 0.5 kg at 260° C.

Advantageously, the imide-linked mono-, bis-, and polymaleimide compounds and compositions of the present invention can be designed to remain as stable and flexible thermoplastic materials at room temperature. These thermoplastic imide-linked maleimides can be compounded with fillers, catalysts, inhibitors, and coupling agents to make a fully formulated adhesive package. Since the matrix of these compositions is thermoplastic, no settling will occur during shipping or storage. These characteristics therefore also permit packaging, shipment and storage without refrigeration. These properties also facilitate forming adhesives of the invention into various shapes and sizes for ease of use and application to electronic components and/or substrates. Thus, one aspect of the invention is a method for forming an adhesive rope that may be applied directly to a substrate for bonding electronic components thereto. According to this method, an imide-linked maleimide compound or adhesive composition is extruded in a rope shape. Unit lengths of the adhesive rope can then be dispensed into a packaging container. The length of adhesive rope dispensed can conveniently be selected by the desired use, application or unit of sale. Thus, a short rope may be packaged for a single-use application while a longer length can be dispensed for bulk sale. In one embodiment of this method, the rope adhesive is a circular, square, or rectangular shape (across the short axis) of about two to 15 millimeters in diameter. One useful shape for the rope adhesive is where the material is extruded in the shape (in cross section) of a four lobbed clover or starfish. The invention also contemplates that other shapes may be manufactured by extrusion or molding, such as ribbons, dots, spheres, and the like. For example, the adhesive may be formed into single-use dots of suitable volume to bond a single electronic component to a substrate. Individual dots may be packaged on a disposable paper or film support and peeled off for use. The dot of adhesive may also be applied in advance to a suitable electronic device substrate (e.g. a lead frame, or ball grid array). Typically, the dots are in the range of 0.5 mm to 10 mm in diameter. A multiple number of dots may also be applied across the bond area of a substrate to accommodate larger devices. The dots may have the form of hemispherical or "Hershey's Kiss-like" shapes.

The present invention also provides methods for bonding an electronic component to a substrate using formed adhesive manufactures such as ropes, ribbons and dots. According to this method, the adhesive manufacture is dispensed directly onto the substrate in an amount sufficient to bond the desired electronic component. For example, a rope can be contacted with the substrate and the desired quantity can be cut from the end, thereby delivering a controlled amount of adhesive to the precise point of desired bonding. Optionally, the substrate can be heated to facilitate delivery of the adhesive by melting. When the amount of adhesive that will be required for a single application can be predetermined at the time of manufacture, individual aliquots of the adhesive can be premeasured, dispensed, and subsequently transferred to the substrate at the time of use, for example as individual dots. Once the adhesive is positioned onto the substrate, the electronic component is then contacted with the dispensed adhesive and the adhesive cured to bond the electronic component to the substrate. This method reduces waste, in that use of excess adhesive is avoided. Furthermore, this method facilitates precise positioning of adhesive and eliminates unwanted adhesive contamination of the substrate and surrounding work area. The thermoplastic nature of these adhesives offers other significant advantages for commercial applications compared to the traditional paste adhesives used for die attach. The materials described here don't require the −40° C. refrigerated storage conditions traditionally used for the paste adhesives. A fully formulated thermoplastic adhesive mixture that contains sufficient inhibitors can be kept for several months at or just below room temperature without any loss of performance. The thermoplastic nature of this adhesive furthermore prevents any settling of the filler from the resin matrix during such storage.

Conveniently, the adhesive compositions of the invention can be packaged into kits for consumption by the end-user. Included in each kit is a package containing a sufficient amount of a curable imide-linked maleimide adhesive composition to bond at least one electronic component to a substrate and instructions for using said adhesive to bond an electronic component to a substrate. The adhesive supplied in the kit may be, for example, in bulk, rope or dot form, depending of the intended end-use. The instructions are contemplated to include directions for preparation of the elements that will be bonded (e.g., electronic components and substrates) application of the adhesive, suggested quantities for various applications, and conditions required to cure the adhesive. The kit format will be particularly useful for maleimide adhesives of the invention with characteristics that may not be well known in the art. For example, techniques for application and curing of adhesive manufactures (e.g., ropes and dots) can be described and illustrated.

Additional embodiments of the invention include adhesive bonded structures containing curable imide-linked maleimide adhesive compositions. Nonlimiting examples of the adhesive bonded structures include electronic components bonded to a substrate, and circuit components bonded to printed wire boards.

In yet another embodiment of the invention, there are provided assemblies of components adhered together employing the above-described adhesive compositions and/or die attach pastes. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method including:

(a) applying the above-described adhesive composition to the first article, (b) bringing the first and second article into intimate contact to form an assembly wherein the first article and the second article are separated only by the adhesive composition applied in (a), and thereafter, (c) subjecting the assembly to conditions suitable to cure the adhesive composition.

Similarly, a microelectronic device can be adhesively attached to a substrate, employing a method including the steps of:

(a) applying the above-described die attach paste to the substrate and/or the microelectronic device, (b) bringing the substrate and the device into intimate contact to form an assembly wherein the substrate and the device are separated only by the die attach composition applied in (a), and thereafter, (c) subjecting the assembly to conditions suitable to cure the die attach composition.

Conditions suitable to cure invention die attach pastes include subjecting the above-described assembly to a temperature of less than about 400° C. for about 0.5 up to 2 minutes. This rapid, short duration heating can be accomplished in a variety of ways, e.g., with an in-line heated rail, a belt furnace, or the like. Optionally, the material can be oven cured at 80-400° C.

In still another embodiment of the invention, there is provided a method for producing an imide-extended bismaleimide monomer. Such a method can be performed, for example, by contacting a dianhydride with a diamine under conditions suitable to form an imide having terminal amino moieties; and contacting the terminal amino moieties with maleic anhydride under conditions suitable to form a maleimide, thereby producing an imide-extended bismaleimide monomer.

It is understood that using the compounds and methods of the present invention, it is possible to prepare adhesives having a wide range of cross-link density by the judicious choice and amount of mono-, bis- or polyfunctional compounds. The greater proportion of polyfunctional compounds reacted, the greater the cross-link density. If thermoplastic properties are desired, the adhesive compositions can be prepared from (or at least contain a higher percentage of) mono-functional compounds to limit the cross-link density. A minor amount of poly-functional compounds can be added to provide some cross-linking and strength to the composition, provided the amount of poly-functional compounds is limited to an amount that does not diminish the desired thermoplastic properties. Within these parameters, the strength and elasticity of individual adhesives can be tailored to a particular end-use application.

The following examples are intended only to illustrate the present invention and should in no way be construed as limiting the subject invention.

EXAMPLES

Example 1

The Synthesis of Imide-Extended Mono-, Bis-, and Polymaleimides

A 500 ml round bottom flask equipped with a Teflon coated stir bar was charged with 250 ml of toluene. Triethylamine, 35 g (0.35 mole) was added to the flask, followed by the slow addition of 35 g (0.36 mole) of anhydrous methanesulphonic acid to form a salt. The mixture was allowed to stir for approximately 10 minutes, followed by the addition of 57 g (0.11 mole) of Versamine 552 (dimer diamine, Cognis Corporation). Pyromellitic dianhydride (10.9 g, 0.05 mole) was slowly added to the stirred mixture. A Dean-Stark trap and condenser were attached to the flask, and the mixture was heated to reflux for 2 hours to form an amine-terminated diimide. The theoretical quantity of water from this condensation had been collected by this time. The reaction mixture was cooled down to room temperature and 12.8 g (0.13 mole) of maleic anhydride was added to the flask, followed by the of 5 g of anhydrous methanesulphonic acid. The mixture was brought to reflux for an additional 12 hours to obtain the expected amount of water. An additional 100 ml of toluene was added to the flask after it had been cooled down to room temperature, and the mixture was then allowed to settle. The solution was decanted, and the salt was rinsed with additional toluene (2×100 ml). The extracts were combined and then again allowed to settle overnight in order to provide sufficient time for additional salt and acid to separate. The solution was filtered through a glass-fritted funnel tightly packed with 30 g of silica gel. The solvent was removed under vacuum to produce 60 g (84% yield) of a dark waxy resin.

Example 2

Similar to the method outlined in the previous example, a salt was formed by mixing 38 g (0.38 mole) of triethylamine with 38 g (0.39 mole) of anhydrous methanesulphonic acid in 250 ml of toluene. Versamine 552, 59 g (0.11 mole) was added to the flask, followed by the slow addition of 16.1 g (0.05 mole) of 3,3',4,4'-benzophenone tetracarboxylic dianhydride. About two of hours of reflux were required for the azeotropic removal of the water to form the amine-terminated diimide. The mixture was cooled down to room temperature, followed by the addition of 12.5 g (0.13 mole) of maleic anhydride and 5 g of methanesulphonic acid. The mixture was refluxed again for 12 hours to form the bismaleimide. The product was worked-up according to the procedure described in the previous example. A dark amber colored resin (65 g, 82% yield) was collected after the complete removal of the solvent.

Example 3

A salt was made by mixing 10 g (0.10 mole) of triethylamine with 11 g (0.11 mole) of methanesulphonic acid in 200 ml of toluene. Versamine 552, 32 g (0.06 mole) was added to the mixture, followed by the slow addition of 13.5 g (0.03 mole) of 1,1,3,3-tetramethyl-1,3-bis(norbornyldicarboxylic anhydride)disiloxane. The amine-terminated diimide was formed after the azeotropic distillation of the water, which required approximately 1 hour of reflux. The mixture was cooled down, followed by the addition of 10 g (0.10 mole) of maleic anhydride along with 3 g of methanesulphonic acid. The mixture was refluxed for 18 hours to collect the required amount of water in the Dean-Stark trap. The work-up of the product was conducted as outlined in the previous examples. The final material (35 g, 73% yield) was obtained as a dark-amber colored resin after the removal of the solvent.

Example 4

A salt was prepared by mixing 40 g (0.40 mole) triethylamine with 40 g (0.42 mole) methanesulphonic acid in 200 ml of toluene. This was followed by the sequential addition of 57 g (0.11 mol) of Versamine 552 and 17 g (0.05 mole) of 2,8-decadiene-1,10-disuccinic anhydride. The mixture was refluxed for 12 hours with azeotropic removal of the water to produce the amine-terminated diimide. The mixture was then cooled down to room temperature and 12.8 g (0.13 mol) of maleic anhydride and 5 g. of methanesulphonic acid were then added to the flask. The mixture was again heated to reflux overnight with azeotropic removal of the water. Work-up of the product gave 65 g (82% yield) of an amber-colored resin.

Example 5

A salt was formed by mixing 35 g. (0.35 mole) of triethylamine with 36 g. (0.37 mole) of methanesulphonic acid in 250 ml of toluene (inside a 500 ml flask). Verasmine 552, 90 g (0.17 mole) was added to the flask, followed by the slow addition of 24 g. (0.11 mole) of pyromellitic dianhydride. About two of hours of reflux were required for the complete azeotropic removal of the water to form the amine-terminated diimide. The mixture was then cooled down to room temperature and 13 g (0.13 mole) of maleic anhydride and 10 g of methanesulphonic acid were then added. The mixture was refluxed again for 12 hours to form the imide-linked bismaleimide. The product was worked up according to the procedure described in the previous example. A dark amber colored resin (100 g, 82% yield) was collected after the complete removal of the solvent.

Example 6

A salt was formed by mixing 50 g (0.50 mole) of triethylamine with 50 g (0.52 mole) of anhydrous methanesulphonic acid in 400 mL of toluene (inside a one liter flask). Bis (aminomethyl)tricyclo[5.2.1.2,6]decane, 33 g. (0.17 mole) was added to the flask, followed by the slow addition of 42 g (0.08 mole) 4,4'-bisphenol-A dianhydride. A couple of hours of reflux were required for the azeotropic removal of the water to form the amine-terminated diimide. The mixture was cooled down to room temperature, followed by the addition of 22 g (0.22 mole) of maleic anhydride and 8 g of methanesulphonic acid. The mixture was refluxed again for 16 hours to form the imide-linked bismaleimide. The product was worked up according to the procedure described in the previous example. The solvent was removed to obtain 80 g (94% yield) of a glassy, light yellow, solid.

Example 7

A salt was formed by mixing 35 g (0.35 mole) of triethylamine with 36 g (0.38 mole) of anhydrous methanesulphonic acid in 400 ml of toluene (inside a 1000 ml flask). Forty-two grams (0.10 mole) of 2,2'-Bis[4-(4-aminophenoxy)phenyl] propane was added to the flask, followed by the slow addition of 11 g (0.05 mole) of pyromellitic dianhydride. About two hours of reflux were required for the azeotropic removal of the water to form the desired amine-terminated diimide. The mixture was cooled down to room temperature, followed by the addition of 8 g (0.08 mole) of maleic anhydride and 8 g of methanesulphonic acid. The mixture was refluxed again for 6 hours to form the bismaleimide. The work-up of the product consisted of removal of the solvent under vacuum, followed by washing the solid on a Buchner funnel with water to remove the salt and acid. A final rinse with acetone was used to remove most of the water. The product was laid out in a shallow pan and dried in a oven overnight at approximately 100° C. A fine yellow powder (44 g, 86% yield) was obtained after drying.

Example 8

A salt was formed by mixing 35 g (0.35 mole) of triethylamine with 36 g (0.38 mole) of anhydrous methanesulphonic acid and 400 ml of toluene (inside a 1000 ml round-bottom flask). Bisphenol-A dianhydride (32 g, 0.06 mole) of was then added to the flask, followed by the addition of 16 g. (0.03 mole) of Versamine 552. The mixture was stirred at room temperature for an hour, followed by the addition of 24 g (0.06 mole) of 2,2'-Bis[4-(4-aminophenoxy)phenyl]propane to the flask. Azeotropic removal of the water was conducted over approximately 20 hours to form the desired amine-terminated imide. The mixture was then cooled down to room temperature, followed by the addition of 10 g (0.10 mol) of maleic anhydride and 5 g of methanesulphonic acid. The mixture was refluxed again for 18 hours to form the imide-extended bismaleimide. The product was worked up according to the procedure described in the previous example. After removal of the solvent, 60 g (82% yield) of a yellow, friable, glassy solid was obtained.

Example 9

A 500 ml round bottom flask equipped with a teflon coated stir bar was charged with 24 g (0.40 mole) of ethylenediamine along with 100 ml of toluene. This was followed by the slow addition of 100 g of polybutadiene grafted with 8% by weight maleic anhydride (RI130MA8, Sartomer). The azeotropic removal of the water and excess ethylenediamine was conducted over a twelve-hour reflux period. The removal of the excess ethylene diamine was aided by the addition of steam into the reaction vessel. The salt (25 g) of triethylamine-methanesulphonic acid was then added to the solution, along with an additional 3 g of methanesulphonic acid and 12 g (0.12 mole) of maleic anhydride. The azeotropic removal of the water was conducted over 12 hours to form the polymaleimide. The work-up of the product was conducted according to the previous examples to obtain 100 g of an amber colored viscous liquid resin.

Example 10

Toluene (350 ml) was added to a one liter round bottom flask equipped with a Teflon coated stir bar. Triethylamine, 50 g (~0.50 mole) was added to the flask followed by the slow addition of 50 g (0.52 mole) of anhydrous methanesulphonic acid. The mixture was allowed to stir at room temperature approximately 10 minutes, followed by the addition of 90 g (0.17 mole) of Versamine 552 (dimer diamine, Cognis Corporation). To the mixture was added 41 g (0.08 mole) of BPADA (4,4'-bisphenol-A dianhydride, GE Plastics). A Dean-Stark trap and condenser were attached to the flask, and the mixture was heated to reflux. After approximately two hours the expected amount of water was collected corresponding to the complete conversion to the amine terminated diimide. The mixture was allowed to cool down to below 40° C., and 22 g (0.23 mole, ~20% excess) of crushed maleic anhydride was added to the flask, followed by the addition of an extra 10 g of anhydrous methanesulphonic acid. The mixture was again slowly heated to reflux. Approximately 18 hours of reflux were required to collect the expected amount of water in the Dean-Stark trap. After cooling down to room temperature an extra 200 ml of toluene was added to the flask; the stirring was stopped at this point and the mixture was allowed to separate. The upper (toluene solution) fraction was carefully decanted into a 2 liter Erlenmeyer flask. The salt was washed with toluene (2×500 ml) the rinses were also decanted and combined. The amber solution was allowed to settle overnight to allow sufficient time for more salt and acid to separate from the combined toluene solution. The solution was then filtered through a glass-fitted funnel tightly packed with 65 g of silica gel. Following filtration the silica gel was washed with an extra 100 ml of toluene. The toluene was removed under reduced pressure to provide 120 g (~85% yield) of a dark amber colored resin.

Example 11

Tensile adhesion testing was done on some of the products from the preceding examples. The only component added to the test resin was 2% by weight of dicumyl peroxide initiator. The catalyzed resin mix was then used to affix aluminum studs to copper slugs. The aluminum posts had a contact head diameter of 290 mils. The copper slugs had dimensions of 1000×400×150 mils. Ten of these test assemblies were constructed for each of the catalyzed resin mixtures. The parts were cured for thirty minutes in an oven at 200° C. The parts were then allowed to cool to room temperature and the adhesive strength was determined using a Sebastian III tensile tester. A control composition was also run along side the test mixtures. The control mix used was the bismaleimide derived from the dimer diamine (i.e. Versamine 552) also catalyzed with 2% dicumyl peroxide.

TABLE 1

Tensile Adhesion Test Results

| Part | Stud Pull Value (pounds force) | |
| --- | --- | --- |
| | Example 10 | Control |
| 1 | 66 | 23 |
| 2 | 54 | 16 |
| 3 | 57 | 15 |
| 4 | 75 | 12 |
| 5 | 47 | 19 |
| 6 | 71 | 9 |
| 7 | 52 | 22 |
| 8 | 70 | 18 |
| 9 | 63 | 8 |
| 10 | 77 | 6 |
| Average | 63 | 15 |
| $F_{n-1}$ | 10 | 6 |

TABLE 2

Tensile Adhesion Test Results

| Part | Stud Pull Value (pounds force) | | | |
| --- | --- | --- | --- | --- |
| | Example 1 | Example 2 | Example 5 | Control |
| 1 | 73 | 97 | 95 | 30 |
| 2 | 59 | 69 | 145 | 15 |
| 3 | 91 | 68 | 103 | 23 |
| 4 | 96 | 77 | 113 | 7 |
| 5 | 98 | 88 | 143 | 21 |
| 6 | 97 | 79 | 156 | 16 |
| 7 | 102 | 81 | 127 | 28 |
| 8 | 60 | 93 | 126 | 24 |
| 9 | 101 | 81 | 113 | 25 |
| 10 | 61 | 71 | 126 | 25 |
| Average | 84 | 80 | 125 | 21 |
| $F_{n-1}$ | 18 | 9.9 | 19 | 6.9 |

The adhesion results for all of the examples shown in Tables 1 and 2 were clearly superior to the control test composition. While not wishing to be bound by theory, it is believed that the improvement seen here is a direct result of the reduced cross-link density and/or reduced cure shrinkage of the invention composition versus the BMI derived solely from the dimer diamine.

Example 12A

SMA EF60 Poly(isophrone maleimide), Method 1

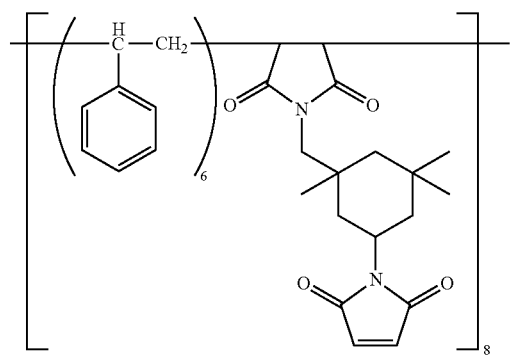

Triethylamine (20 g, 198 mmol), methanesulfonic acid (25 g, 260 mmol), toluene (200 ml), and a stir bar were added to a 1-neck, 1 L flask. A trap and condenser were attached to the flask. This mixture was refluxed for an hour to remove residual water. Cumene end-capped styrene maleic anhydride (72.5 g, 100 meq, "SMA EF60" available from Sartomer) was dissolved into the stirred mixture while it was still warm. The solution was cooled to room temperature. Isophorone diamine (20.4 g, 120 mmol) was then dripped in slowly to the stirred solution. Solids separated from the solution during this addition. The solution had to be manually swirled towards the end of the diamine addition. Once the diamine addition was complete, maleic anhydride (17.7 g, 180 mmol) was added and the flask was manually swirled until the anhydride was completely dissolved. The addition of the anhydride transformed the solution to a bright yellow color. Butylated hydroxytoluene (BHT, 75 mg) was added to the flask. A Dean-Stark trap and condenser were attached to the flask and the mix was then stirred and refluxed for 69 hours to collect 3.7 ml of water from the condensation of the amic acid residues. Toluene (200 ml) was stirred into the cooled mixture. The mix was allowed to settle and the upper toluene phase was decanted. Additional portions of toluene (4×50 ml) were used to extract the product from the lower phase. The combined toluene extracts were allowed to settle overnight and then decanted once again into a clean flask. The toluene phase was passed over a bed of 30 g of silica gel in a fritted funnel. The toluene was removed via rotary evaporation followed by air sparge. The recovered solids were dissolved in acetone (300 ml) and precipitated into deionized water (2 L). 56.0 grams of an off-white solid was collected. A portion of this product was catalyzed with 2% by weight dicumyl peroxide and then subjected to thermogravimetric analysis (TGA). The retained weight at 300° C. (TGA ramp rate=10° C./min., air purge) was 97.7% and the decomposition onset was at 381° C. A DSC (differential scanning calorimeter) run was conducted (ramp rate=10° C./min., air purge) on the compound (again catalyzed with 2% by weight dicumyl peroxide). A cure exotherm was observed to occur with an onset of 156.8° C., cure maxima at 172.6° C. and cure energy of 31.3 J/g. An infrared spectrum of the neat material included absorptions at 2926, 1855, 1779, 1709, 1601, 1493, 1453, 1360, 1220, 1154, 1078, 1030, 920, 829, 759, and 699 wavenumbers. Thermomechanical analysis (TMA) was conducted on a cured slug of this compound. The cured resin was found to have an $\alpha_1$=56.7 ppm/° C., an $\alpha_2$=225.0 ppm/° C. and a $T_g$=148.6° C.

Example 12B

SMA EF60 Poly(isophrone maleimide), Method 2

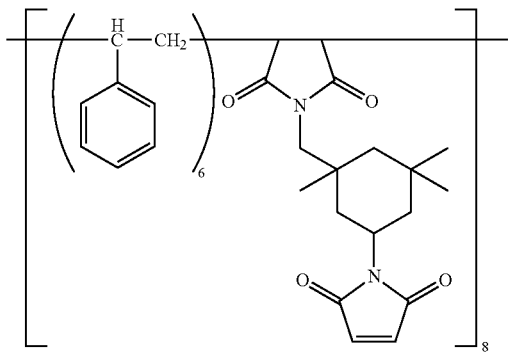

The same molecule as shown in Example 1a was made using a different method. The styrene maleic anhydride copolymer (72.5 g, 100 meq, "SMA EF60" available from Sartomer) was dissolved in toluene (250 ml) in a 1 L flask. N-methyl-2-pyrrolidone (60 ml) and a stir bar were added to the flask. A trap and condenser were then attached to the flask. This mixture was refluxed for 45 minutes to remove all residual water. This toluene-NMP solution was then dripped into a solution of isophorone diamine (20.4 g, 120 mmol) dissolved in toluene (100 ml). Halfway through the addition of NMP, the solution became too thick to stir. It had to be manually swirled as the toluene-NMP solution continued to drip in. Additional NMP (30 ml) was added. Methanesulfonic acid (5.0 g) and maleic anhydride (17.7 g, 180 mmol) were then also added to the flask. The mix was, at this point, a very viscous, gelatinous mass. The flask was rotated in a water bath for 2 hours in a 75° C. bath to complete the dissolution of the maleic anhydride. The flask was then fitted with a trap and condenser. The solution was stirred and refluxed for 50 hours. A total of 4.9 ml of water was collected. Toluene (100 ml) was added to the flask. The solution was neutralized with sodium bicarbonate (15 g) and water (5 g). It was then dried with magnesium sulfate (15 g) and passed over silica gel (35 g). The toluene was removed via rotary evaporation and air sparge. The solids were dissolved in acetone (300 ml) and precipitated into deionized water (2 L). A total of 95.1 grams of a beige solid was recovered after the collected solids had been dried. A sample of this compound was catalyzed with 2% by weight dicumyl peroxide and subjected to thermogravimetric analysis (TGA). The retained weight at 300° C. (TGA ramp rate=10° C./min., air purge) was 97.0% and the decomposition onset was at 396° C. A DSC (differential scanning calorimeter) run was conducted (ramp rate=10° C./min., air purge) on a sample of this material that was catalyzed with 2% by weight dicumyl peroxide. A cure exotherm was observed to occur with an onset of 141.7° C., cure maxima at 164.9° C. and cure energy of 74.7 J/g. Infrared spectrum included absorptions at 2922, 1778, 1710, 1601, 1494, 1453, 1404, 1359, 1220, 1148, 1090, 918, 829, 759, and 697 wavenumbers. A TMA was conducted on a cured slug of this compound. The cured resin was found to have an $\alpha_1$=58.9 ppm/° C., an $\alpha_2$=185.0 ppm/° C. and a $T_g$=146.0° C.

Example 13

SMA EF60 Poly(2,6,2',6'-methylenedianiline maleimide)

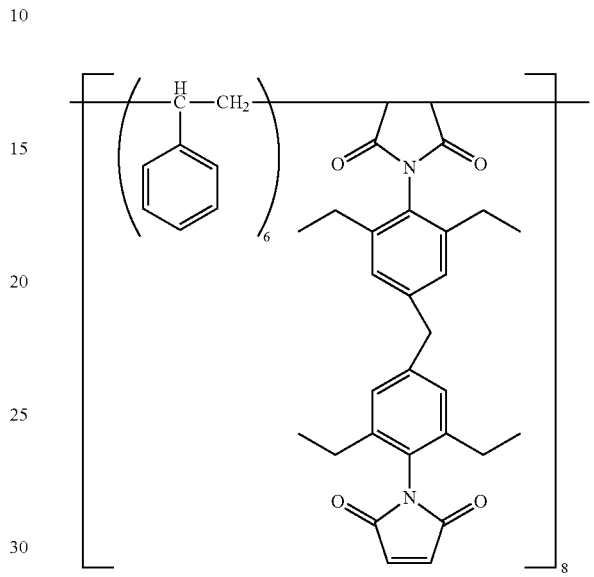

4,4'-Methylenebis(2,6-diethylaniline) (20.2 g, 65 mmol) was dissolved in NMP (10 ml) and toluene (160 ml). The solution was refluxed to azeotrope off any residual water. Once the solution had been cooled to room temperature, maleic anhydride (9.8 g, 100 mmol) was dissolved in, turning the solution a cherry red. Cumene end-capped styrene maleic anhydride (21.8 g, 30 meq, "SMA EF60" available from Sartomer) was dissolved in next. The addition of the "SMA EF60" did not result in any further change in color or viscosity. The solution, however, became a purplish red after the addition of methanesulfonic acid (3.0 g). The solution was refluxed for 2.75 hours and 2.4 ml of water was collected. Toluene (100 ml) was added to the flask. The solution was then subjected to repeated brine extractions (6×25 ml). The toluene phase was dried with magnesium sulfate (20 g) and passed over silica gel (30 g). The toluene was removed via rotary evaporation and air sparge. The residue was dissolved in acetone (150 ml) and precipitated into ice-cold deionized water (1.5 L). A total of 95.1 grams of an amber, glassy, powdered solid was recovered. A portion of this compound was catalyzed with 2% by weight dicumyl peroxide and subjected to thermogravimetric analysis (TGA). The retained weight at 300° C. (TGA ramp rate=10° C./min., air purge) was 96.5% and the decomposition onset was at 409° C. A DSC (differential scanning calorimeter) run was conducted (ramp rate=10° C./min., air purge) on a sample of this material that was catalyzed with 2% by weight dicumyl peroxide. A cure exotherm was observed to occur with an onset of 153.2° C., cure maxima at 186.4° C. and cure energy of 82.6 J/g. Infrared spectrum included absorptions at 2967, 1778, 1712, 1601, 1453, 1376, 1220, 1151, 1060, 952, 828, 759, and 700 wavenumbers. Thermomechanical analysis (TMA) was performed on a cured slug of this polymaleimide compound.

The cured resin was found to have an $\alpha_1$=60.0 ppm/° C., an $\alpha_2$=187.6 ppm/° C. and a $T_g$=119.1° C.

Example 14

SMA 2000P Poly(isophrone maleimide)

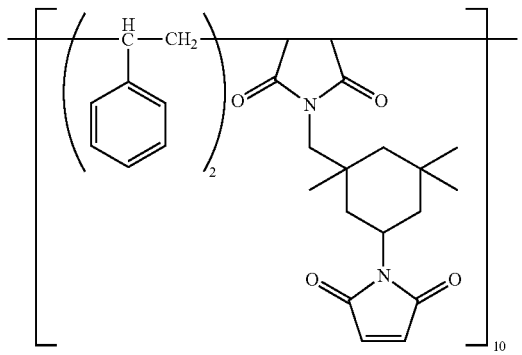

Cumene-capped styrene maleic anhydride resin (30.6 g, 100 meq, "SMA 2000P" available from Sartomer) was dissolved in heated N-methyl-2-pyrrolidone (60 ml). The solution was allowed to cool to room temperature and was then dripped into isophorone diamine (20.4 g, 120 mmol) dissolved in toluene (180 ml). The mixture stirred for an additional ten minutes. Methanesulfonic acid (5.0 g) was then added. The solution was refluxed for half an hour to remove residual water. Once the solution had cooled, maleic anhydride (15.7 g, 160 mmol) and BHT (108 mg) were added. As the components mixed into the solution, it became a fairly thick slurry. The slurry solids dissolved and the mixture transformed into a clear solution upon reflux. The solution was refluxed for 34 hours. A total of 4.5 ml of water was collected in the trap at the end of this period. Toluene (200 ml) was added. The solution was neutralized with sodium bicarbonate (10 g) and water (5 g). It was dried with magnesium sulfate (10 g), and then passed over silica gel (25 g). The toluene was removed via rotary evaporation followed by air sparge. The residue was dissolved in acetone (250 ml) and precipitated into deionized water (1.5 L). The solids were filtered and dried and then re-dissolved in acetone (300 ml). The acetone solution was then precipitated again in deionized water (2 L). The solids were filtered and dried overnight in a 75° C. oven. A total of 55.1 grams (90.8% theory) of a fine, buff, powder was collected. A portion of this compound was catalyzed with 2% by weight dicumyl peroxide and subjected to thermogravimetric analysis (TGA). The retained weight at 300° C. (TGA ramp rate=10° C./min., air purge) was 93.7% and the decomposition onset was at 364° C. A DSC (differential scanning calorimeter) run was also conducted (ramp rate=10° C./min., air purge) on a sample of this material (again, catalyzed with 2% by weight dicumyl peroxide). A cure exotherm was observed to occur with an onset of 156.2° C., a cure maxima at 168.0° C., and a cure energy of 86.5 J/g. An infrared spectrum on this compound revealed prominent absorptions at 2927, 1778, 1704, 1601, 1371, 1220, 1146, 920, 829, 762, and 696 wavenumbers. A TMA test was performed on a cured slug of this compound. The cured resin was found to have an $\alpha_1$=48.7 ppm/° C., an $\alpha_2$=88.1 ppm/° C. and a $T_g$=183.6° C.

Example 15

SMA EF30 Poly(isophrone maleimide)

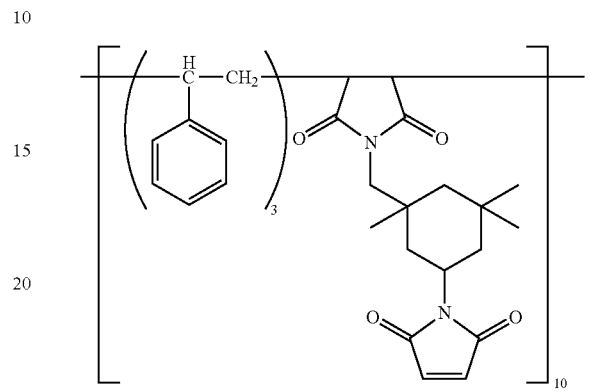

Cumene end-capped styrene maleic anhydride resin (41.0 g, 100 meq, "SMA EF30" available from Sartomer) was not soluble in warm N-methyl-2-pyrrolidone (60 ml), so heated toluene (60 ml) was added to dissolve the resin. This solution was dripped into isophorone diamine (20.4 g, 120 mmol) in toluene (120 ml). The mixture became a slurry, but was still fluid enough to be stirred magnetically for an hour at room temperature. As the mixture continued stirring at room temperature, it did become thicker, so additional toluene (50 ml) was added. The mixture was then stirred in a 60° C. water bath for an hour. Methanesulfonic acid (5.0 g) and maleic anhydride (17.7 g, 180 mmol) were added and to the flask. A trap and condenser were attached and the mixture was then refluxed for 48 hours. A total of 4.9 ml of water was collected. The solution was then diluted with toluene (200 ml), and neutralized with sodium bicarbonate (15 g) and water (5 g). The solution was dried with magnesium sulfate (15 g) and passed over silica (30 g). The toluene was removed via rotary evaporation followed by air sparge. The residue was dissolved in acetone (250 ml) and precipitated into deionized water (1.6 L). The precipitate was filtered and dried in a 75° C. oven. A total of 69.6 grams (97.9% theory) of a buff colored powder was collected. A portion of this compound was catalyzed with 2% by weight of dicumyl peroxide and subjected to TGA (10° C. per minute ramp, air purge). The retained weight at 300° C. (TGA ramp rate=10° C./min., air purge) was 96.1% and the decomposition onset was at 407° C. A DSC (differential scanning calorimeter) run was conducted (ramp rate=10° C./min., air purge) on a sample of this material (again catalyzed with 2% by weight dicumyl peroxide). A cure exotherm was observed to occur with an onset of 150.0° C., cure maxima at 161.1° C. and cure energy of 111.3 J/g. Prominent infrared spectrum absorptions included 1777, 1695, 1601, 1453, 1404, 1363, 1220, 1146, 921, 829, 761, and 697 wavenumbers. A TMA was conducted on a cured slug of the cured compound from this example. The cured resin was found to have an $\alpha_1$=53.0 ppm/° C., an $\alpha_2$=119.1 ppm/° C. and a $T_g$=198.1° C.

Example 16

SMA EF40 Poly(isophrone maleimide)

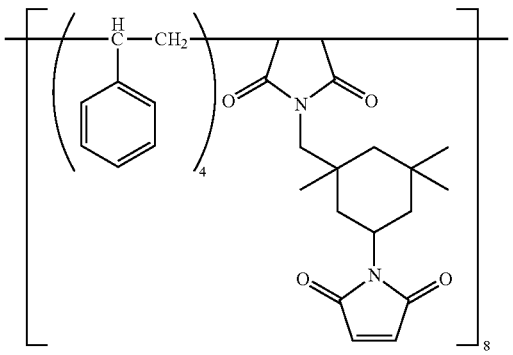

Cumene end-capped styrene maleic anhydride resin (51.7 g, 100 meq, "SMA EF40" available from Sartomer) was dissolved in a mixture of N-methyl-2-pyrrolidone (60 ml) and toluene (150 ml). This solution was refluxed (with a trap and condenser attached) to remove any residual water. When cool, this dried solution was dripped into a solution of isophorone diamine (20.4 g, 120 mmol) dissolved in toluene (100 ml). The mixture became too thick to stir magnetically, so it had to be swirled manually during the final stage of the addition. Methanesulfonic acid (5.0 g) and maleic anhydride (17.7 g, 180 mmol) were then added to the flask. The mix was swirled for 25 minutes. BHT (75 mg) was added. A trap and condenser were again attached to the flask and reflux of this stirred mixture was conducted for 56 hours. A total of 4.4 ml of water was collected. The cooled solution was diluted with toluene (200 ml) and then neutralized with sodium bicarbonate (15 g) and water (5 g). The solution was dried with magnesium sulfate (15 g) and then passed over silica (30 g). The toluene was removed via rotary evaporation followed air sparge. The residue was dissolved in acetone (250 ml) and precipitated into deionized water (1.6 L). The precipitate was filtered and dried in a 75° C. oven. A total of 79.2 grams (97% theory) of buff colored powder was collected. A portion of this compound was catalyzed with 2% by weight dicumyl peroxide and subjected to a TGA. The retained weight at 300° C. (TGA ramp rate=10° C./min., air purge) was 96.3% and the decomposition onset was at 414° C. A DSC (differential scanning calorimeter) run was conducted (ramp rate=10° C./min., air purge) on a sample of the compound (again catalyzed with 2% by weight dicumyl peroxide). A cure exotherm was observed to occur with an onset of 151.7° C., cure maxima at 168.2° C., with a energy of 160.4 J/g. Significant infrared spectrum absorptions included 2925, 1778, 1704, 1494, 1377, 1220, 1146, 921, 829, 760, and 697 wavenumbers. The cured resin was found to have an $\alpha_1$=52.0 ppm/° C., an $\alpha_2$=125.4 ppm/° C. and a $T_g$=153.2° C.

Example 17

Imide-Extended Hindered BMI

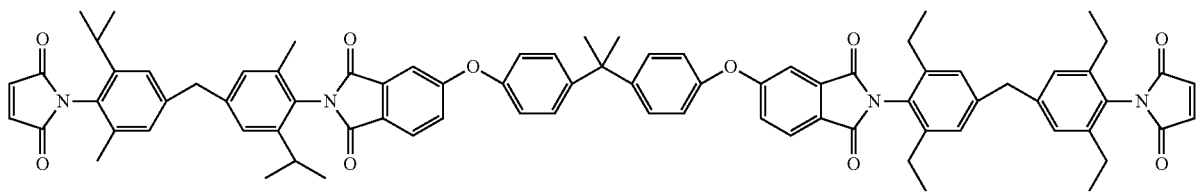 [SMILES: CCc1cc(Cc2cc(CC)c(N3C(=O)c4ccc(Oc5ccc(C(C)(C)c6ccc(Oc7ccc8c(c7)C(=O)N(c7c(C)cc(Cc9cc(C)c(N%10C(=O)C=CC%10=O)c(C(C)C)c9)cc7C(C)C)C8=O)cc6)cc5)cc4C3=O)c(CC)c2)cc(CC)c1N1C(=O)C=CC1=O]

A 500 ml, 1-neck flask was charged with 26.0 g (0.050 mmole) Bisphenol A dianhydride (GE Plastics), 9.8 g (0.10 mole) maleic anhydride, and 200 ml toluene. This mixture was stirred magnetically and heated to 75° C. to form a solution/slurry. A solution consisting of Lonzacure M-DEA and Lonzacure M-MIPA (15.53 g, 0.050 mole, each) dissolved in 50 ml toluene was added to the hot solution. A gooey, purple solid precipitated out of solution during this addition, but this did not interfere with the stirring. Methanesulfonic acid (2.0 g) was added to the flask. A Dean-Stark trap and condenser were attached to the flask the mixture was refluxed for 4 hours to collect 3.6 ml (equal to theory) water. The toluene solution was a homogeneous, clear amber liquid at the end of the reflux period. The solution was cooled, diluted with toluene (100 ml) and then neutralized with sodium bicarbonate (10 g) and water (3 g). The solution was dried with magnesium sulfate (8 g) and then passed over silica (15 g). The bulk of the toluene was removed via rotary evaporation followed air sparge. The product became too viscous to remove the last traces of toluene using a water bath, so the final air sparge was conducted using an oil bath to heat the flask to 120° C. A total of 58.76 g (92.9% of theory) of a clear, amber, glassy solid was recovered. A TGA was run on the neat compound which revealed a retained weight at 300° C. (TGA ramp rate=10° C./min., air purge) was 98.9% and a decomposition onset at 501.8° C. Significant infrared spectrum absorptions for this compound included 2966, 1776, 1710, 1600, 1475, 1372, 1233, 1153, 1103, 829, and 691 wavenumbers.

Example 18

Imide-Extended Hindered BMI

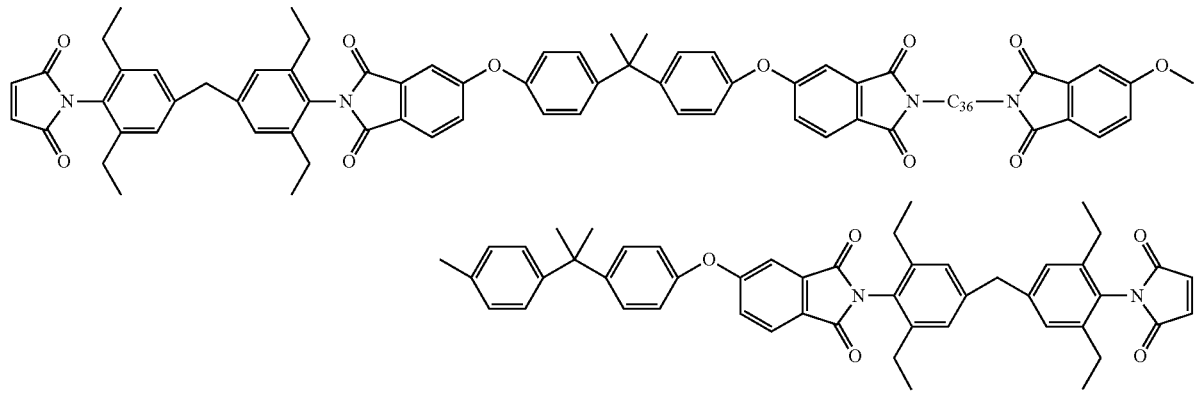

Bisphenol A dianhydride (26 g, 50 mmol, available from Sabic Innovative Plastics) was dissolved in toluene (100 ml) in a 3-neck, 500 ml flask. A stir bar was added to the flask. One neck was equipped with a temperature controller probe. Another neck was equipped with a Dean-Stark trap and condenser. The third neck was equipped with an addition funnel. The temperature was set to 75° C. Versamine 552 (13.4 g, 25 mmol, Cognis Corporation) was diluted in toluene (50 ml). This solution was dripped into the stirred mixture via the addition funnel. Afterwards, 4,4'-methylenebis(2,6-diethylaniline) (15.5 g, 50 mmol, available from Lonza Group of Switzerland) was dissolved in toluene (50 ml) and dripped into the solution. The mixture refluxed for 2.5 hours. 1.8 ml $H_2O$ (equivalent to theoretical) was collected. The mixture was cooled and maleic anhydride (5.4 g, 55 mmol) plus methanesulfonic acid (2 g) were added to the flask. The solution was refluxed for 4 hrs and another 1.0 ml of water was collected. The solution was washed with sodium bicarbonate, treated with $MgSO_4$ and then passed over $SiO_2$. Removal of toluene by rotary evaporation followed by heating the product in a vacuum oven at 100° C. afforded the corresponding bismaleimide in 86% yield. The product was a clear, amber, glassy solid. The neat BMI compound was subjected to thermogravimetric analysis (TGA). The retained weight at 400° C. (TGA ramp rate=10° C./min., air purge) was 98.4% and the decomposition onset was at 479° C. Infrared spectrum included absorptions at 3026, 2968, 2922, 2856, 1774, 1711, 1600, 1472, 1370, 1234, 1105, 1015, 832, and 693 wavenumbers.

Example 19

Imide-Extended Hindered BMI

Bisphenol A dianhydride (26 g, 50 mmol) was dissolved in toluene (100 ml) in a 3-neck, 500 ml flask. A stir bar was added to the flask. One neck was equipped with a temperature controller probe. Another neck was equipped with a Dean-Stark trap and condenser. The third neck was equipped with an addition funnel. The temperature was set to 75° C. 4,4'-Methylenebis(2,6-diethylaniline) (23.3 g, 100 mmol) was dissolved in toluene (100 ml) and dripped into the stirred solution of dianhydride. The mixture refluxed for 3.3 hours and 1.9 ml of water (theoretical was 1.8 ml) was collected. The mixture was cooled and maleic anhydride (10.8 g, 110 mmol) plus methanesulfonic acid (2.5 g) were added to the flask. The solution refluxed for 49 hrs and 1.1 ml of water was collected in the trap. The solution was neutralized with sodium bicarbonate (10 g+3 g $H_2O$), then dried with $MgSO_4$ (8 g), and finally passed over SiO$_2$ (20 g). The toluene was removed via rotary evaporation and air sparge. Residual toluene was removed in a vacuum oven (set at approximately 160° C.). The product was a clear, amber solid that weighed 48.2 g. The BMI compound was subjected to thermogravimetric analysis (TGA). The retained weight at 400° C. (TGA ramp rate=10° C./min., air purge) was 99.9% and the decomposition onset was at 521° C. Infrared spectrum included absorptions at 3029, 2969, 2874, 1775, 1710, 1601, 1476, 1369, 1236, 1101, 1014, 827, and 694 wavenumbers.

Example 20

Imide-Extended TMH-BMI

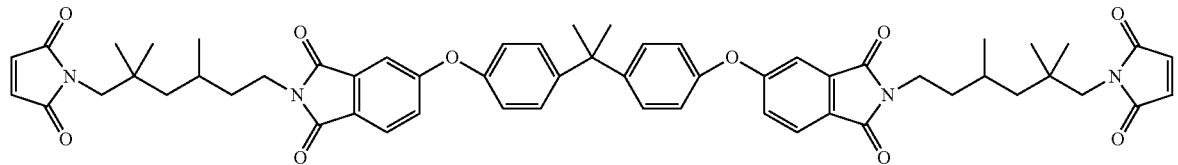 [SMILES: CC(CCN1C(=O)c2ccc(Oc3ccc(C(C)(C)c4ccc(Oc5ccc6c(c5)C(=O)N(CCC(C)CC(C)(C)CN5C(=O)C=CC5=O)C6=O)cc4)cc3)cc2C1=O)CC(C)(C)CN1C(=O)C=CC1=O]

Triethylamine (20 g), methanesulfonic acid (25 g), and toluene (200 ml) were added to a 1-neck, one-liter flask. The mix was refluxed to remove any residual water. When cool, bisphenol A dianhydride (52 g, 100 mmol) and maleic anhydride (19.6 g, 200 mmol) were added to the flask. When the solids had completely dissolved, 2,2,4-trimethyl-1,6-hexanediamine (31.7 g, 200 mmol) was dripped in. The mix was refluxed for 24 hours to collect 7.1 ml of water (theoretical was 7.2 ml). Toluene (100 ml) and water (25 ml) were added to the cooled solution. Toluene extractions (4×50 ml) were used to extract the toluene soluble product from the inorganic phase. The collected toluene fractions were dried with magnesium sulfate (15 g) and passed over a bed of silica gel (2×25 g). The toluene was removed via rotary evaporation and air sparge. Residual toluene was removed in a vacuum oven (oven temperature was ~125° C.). The product was an amber, friable, glassy solid that weighed 58.8 g. The BMI compound was subjected to thermogravimetric analysis (TGA). The retained weight at 400° C. (TGA ramp rate=10° C./min., air purge) was 97.1% and the decomposition onset was at 469° C. Infrared spectrum included absorptions at 3459, 3095, 2962, 1769, 1709, 1601, 1504, 1443, 1367, 1266, 1230, 1172, 1014, 888 and 695 wavenumbers.

Example 21

Imide-Extended Liquid BMI

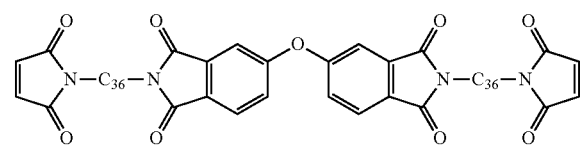

Triethylamine (20 g), methanesulfonic acid (25 g), and toluene (200 ml) were added to a 1-neck, 1 L flask. The mix was refluxed to remove any residual water. Oxydiphthalic anhydride (15.5 g, 50 mmol, available from Sabic Innovative Plastics) was added to the salt mix. The anhydride did not dissolve completely, even with warming. Versamine 552 (53.6 g, 100 mmol) was added over the course of 10 minutes (which resulted in an exotherm). The mixture was refluxed for 14.5 hrs and 1.9 ml of water (theoretical=1.8 ml) was collected. When the solution cooled, maleic anhydride (10.8 g, 110 mmol) was dissolved in. The solution was then refluxed for 27 hours and 1.7 ml of water (theoretical=1.8 ml) was collected. Toluene (6×100 ml) was used to extract the product from the triethylamine—methanesulfonic acid phase. The collected toluene phase was passed over silica gel (30 g). The toluene was removed via rotary evaporation followed by a sparge with clean, dry air. The product was a clear, red, viscous liquid. The BMI compound was subjected to thermogravimetric analysis (TGA). The retained weight at 400° C. (TGA ramp rate=10° C./min., air purge) was 99.4% and the decomposition onset was at 474° C. Infrared spectrum included absorptions at 2922, 2851, 1771, 1708, 1609, 1441, 1393, 1366, 1272, 1233, 826, 747, and 696 wavenumbers.

Example 22

Maleimide-Capped Poly(amide-imides)

Poly(amide-imide) bismaleimides are a new class of thermoset resins that are similar to the imide-linked maleimides, with one exception in that they also have an amide linker in the molecule. This amide linker is produced via the reaction of a carboxylic acid with an isocyanate. When cured these materials should offer the advantage of giving a tougher plastic in certain circumstances and they also tend to be more soluble in a wider variety of organic solvents than many of the imide-linked maleimides.

The synthesis of these materials is conducted in a one-pot procedure in a polar aprotic solvent along with acid catalyst. The first part of the reaction is to produce an anhydride-capped polyimide. The reaction of a diamine with excess dianhydride coupled with azeotropic distillation of the water co-product produces this intermediate.

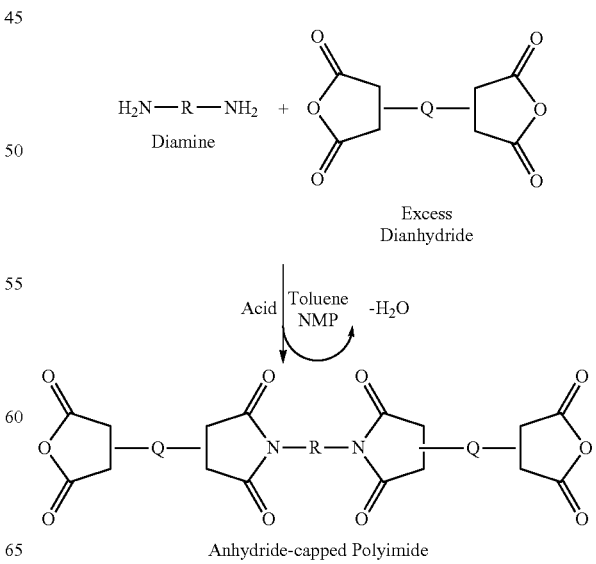

The anhydride-capped polyimide is then reacted with two equivalents of an amino acid to give a carboxyl-capped polyimide after further azeotropic distillation of the water co-product.

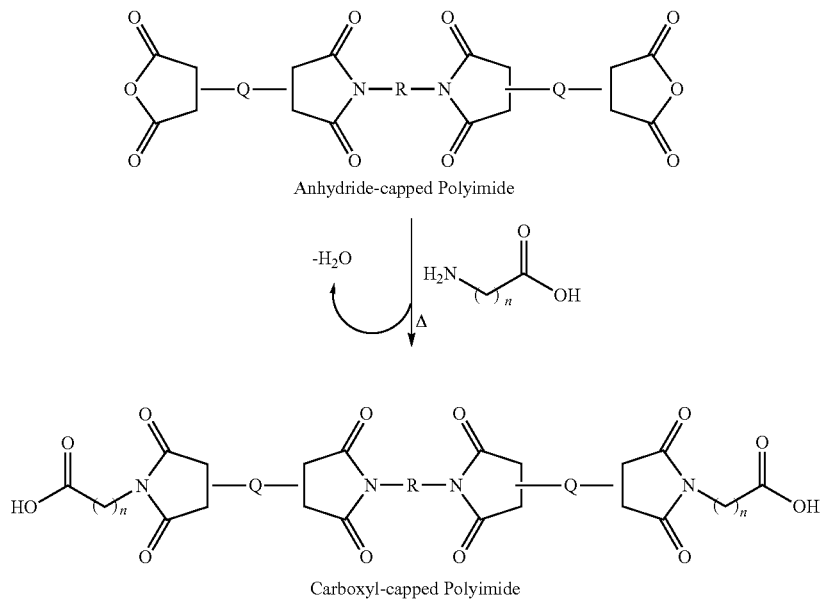

Anhydride-capped Polyimide

Carboxyl-capped Polyimide

The carboxyl-capped polyimide is then reacted with excess diisocyanate. This is a classic reaction that is known to produce amide and give off carbon dioxide gas as a byproduct. The reaction at this point has produced an isocyante-capped poly(amide-imide).

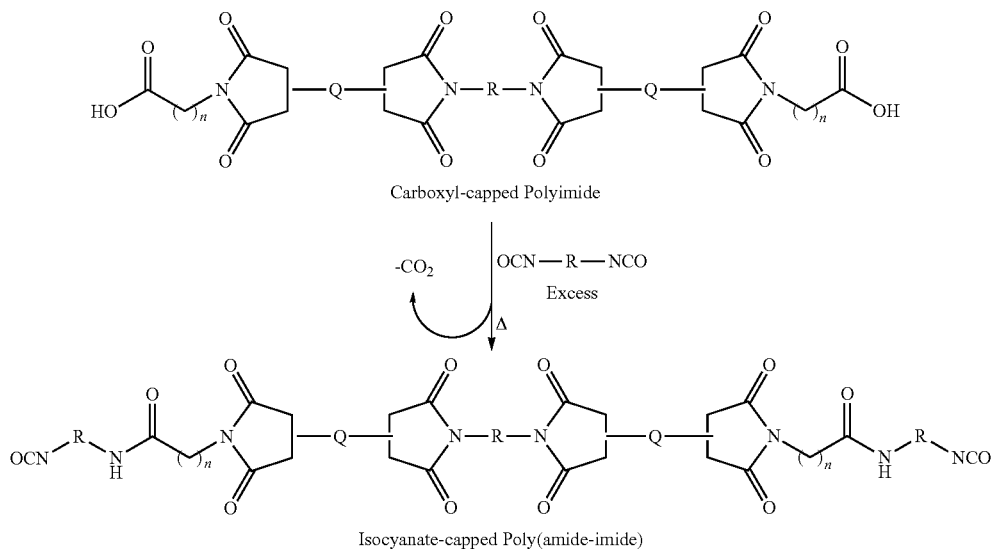

Carboxyl-capped Polyimide

Isocyanate-capped Poly(amide-imide)

Reacting the isocyante-capped poly(amide-imide) with a functionalized carboxylic acid such as a maleimido-acid produces the final product, along with further evolution of carbon dioxide. The finished product, which is a maleimide-capped poly(amide-imide), is isolated by precipitation in an appropriate solvent such as acetone or methanol to remove the NMP and any residual acid contaminants.

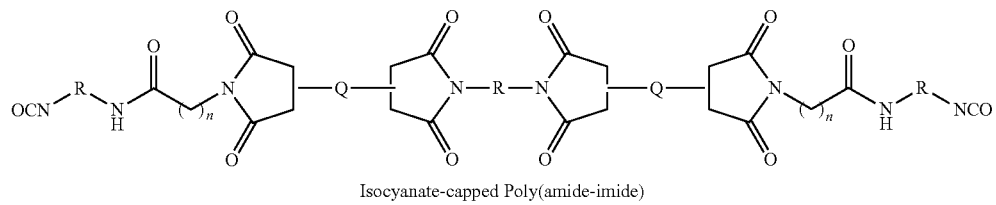

Isocyanate-capped Poly(amide-imide)

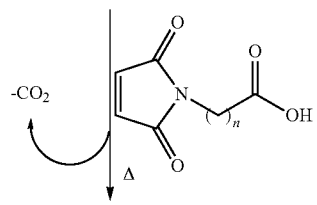

Maleimide-capped poly(amide-imide)

A specific example of a maleimide-capped poly(amide-imide) is the following. In this case a combination of two different dianhydrides was used to produce a lower melting molecule. The polyimide portion was synthesized using four equivalents of dianhydride and three equivalents of diamine. Subsequently, the polyimide was reacted with two equivalents of 6-aminocaproic acid, followed by the reaction with 2-equivalents of a diisocyanate (TMDI). The final step was the addition of 6-maleimidocaproic acid to produce the final product. A representative structure for the targeted poly (amide-imide) BMI compound is shown below.

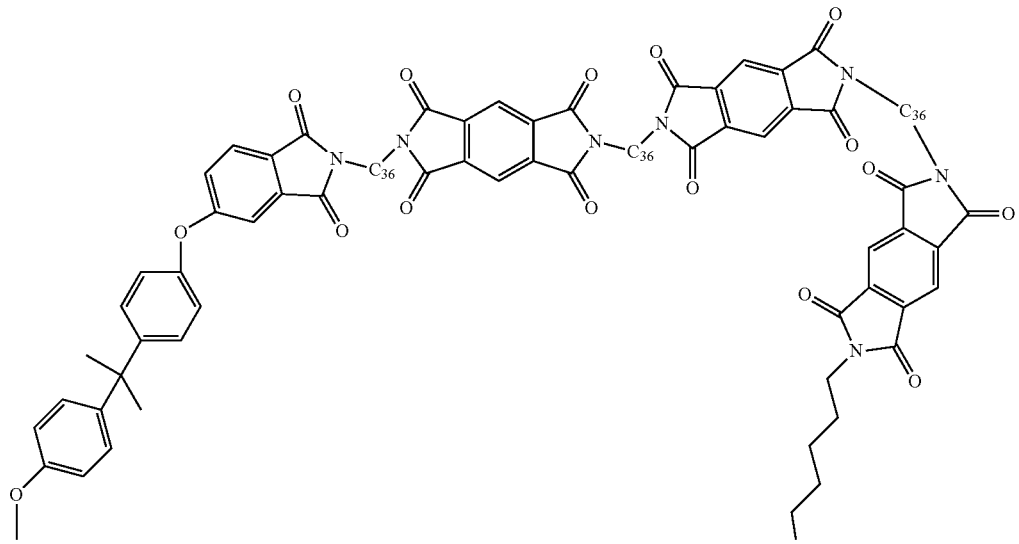

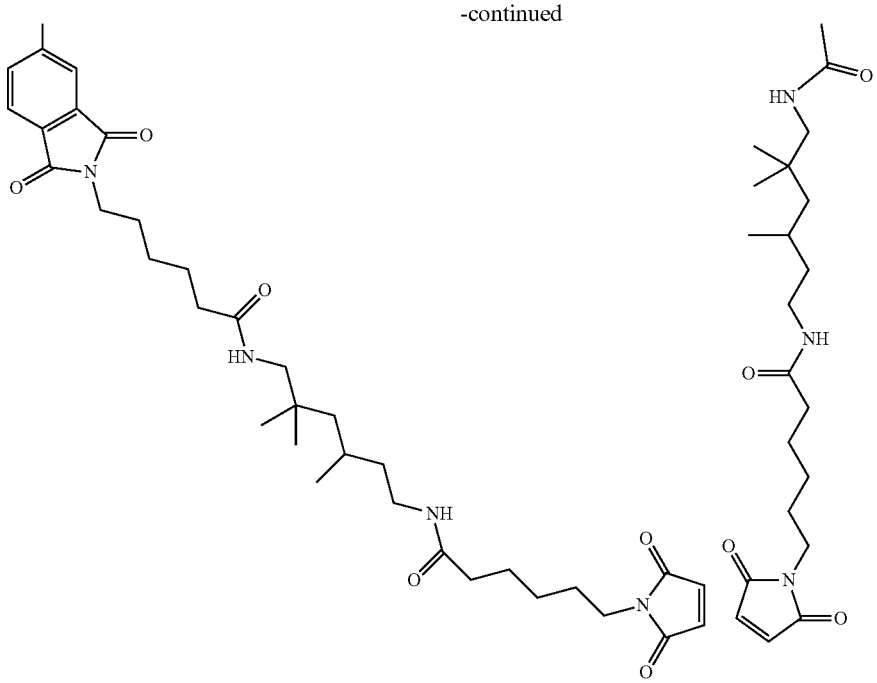

Procedure:

A 2-L reaction flask, equipped with a Teflon-coated stir bar, and reflux condenser was assembled. To the flask was added 300 mmol (65.4 g) of pyromellitic dianhydride along with 100 mmol (52.0 g) of bisphenol-A dianhydride. A solvent mixture was added to the flask composed of 500 g of NMP and 150 g of toluene. The mixture was stirred until the solids were completely dissolved. This was followed by the addition of 50 g of anhydrous methanesulfonic acid. Slowly, 300 mmol (160.8 g) of Versamine-552 was added to the stirred mixture using a dropping funnel over 30 minutes to form the polyamic acid. A Dean-Stark trap was attached to the flask and the material was heated to reflux to remove the water that is condensed in the reaction. After 3 hours of reflux the solution was cooled down and 200 mmol (26.2 g) of 6-aminocaproic acid was added to the flask. The solution was heated again to reflux for 3 hours to azeotrope the water from the imidization reaction. Once the water stops coming off, the heat is turned off and the solution is cooled down below boiling. At this point 200 mmol (42.0 g) of TMDI is added to the solution, and heated to reflux. The $CO_2$ generated in the reaction is observed by attaching an oil bubbler to the reflux condenser. After several hours of reflux, the $CO_2$ stops being generated signaling the end of the reaction. The solution is cooled once again and 250 mmol (52.7 g) of 6-maleimidocaproic acid is added to the solution. The solution was then heated to reflux overnight to complete the amide formation. The cooled solution was transferred to a dropping funnel and slowly added to 2 gallons of stirred acetone to precipitate the solid product. The solid was filtered through a Buchner funnel and washed with acetone to wash out any remaining NMP and acid. The solid was then placed in an oven at 40° C. to dry the product. Approximately 300 g of product was isolated, which was about an 84% yield.

Example 23

Polypropylene and Polyethylene Compounds with Pendent Maleimides

Westlake Chemical Corporation and other companies offer several different maleated polyethylene and maleated polypropylene compounds. These are relatively low molecular weight polymers that may have branching to help solubility and also have different amounts of maleic anhydride reacted with them to give the maleated product. These maleated polyolefins can be used as very hydrophobic, low modulus substrates to produce compounds with pendent maleimide groups.

Figure 4:
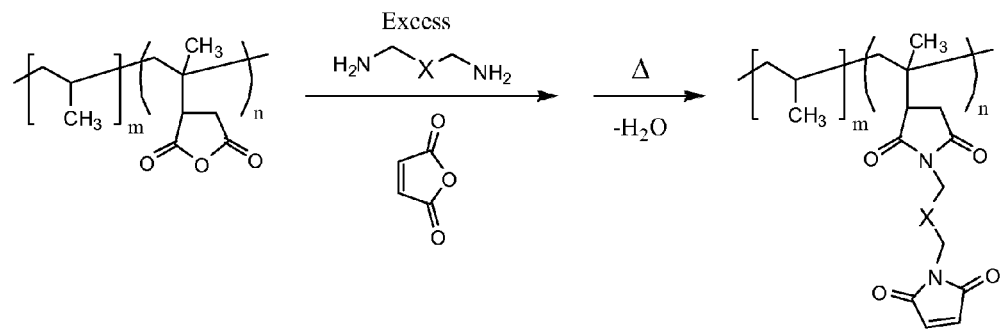
FIG. 4 illustrates the synthesis of polymaleimide of polypropylene-graft-maleic anhydride.

In one specific case a polypropylene-graft-maleic anhydride was used that was purchased from Aldrich. This material has an average molecular weight $M_W$ of approximately 9100, and is approximately 10% maleated. The material, which is supplied in pellet form, was dissolved in a mixture of toluene and NMP and was converted to the maleimide (FIG. 4) according to the following procedure.

Procedure:

A 1-L reaction flask equipped with a Teflon-coated stir bar, Dean-Stark trap and condenser was assembled. To the flask was added 50 g of the polypropylene-graft-maleic anhydride along with 400 mL of toluene and 100 mL of NMP. The mixture was heated to 50-60° C. and stirred on a hot plate to completely dissolve the polymer. Once the polymer was dissolved, 100 mmol of Versamine-552 (53.6 g, which was a large excess based on the number of equivalents anhydride present) was added to the flask and stirred to form the polyamic acid. The solution was heated to reflux for two hours to remove the small amount of water produced in the reaction (<1 mL). The solution was cooled down below 50° C. and 200 mmol (19.6 g) of maleic anhydride was added to the flask along with 10 g of anhydrous methanesulfonic acid. The solution was heated to reflux overnight to complete the conversion to the maleimide. After 16 hours of reflux, approximately 4 mL of additional water and NMP was collected in the Dean-Stark trap. The solution was cooled down, and transferred to a dropping funnel. The solution was slowly added to 2-L of stirred acetone to precipitate the product. The mixture was filtered through a Buchner funnel and the solid was continually washed with acetone to remove all impurities. Approximately 52 g of a white powder was collected after drying in the oven at 50° C. overnight.

Figure 5:
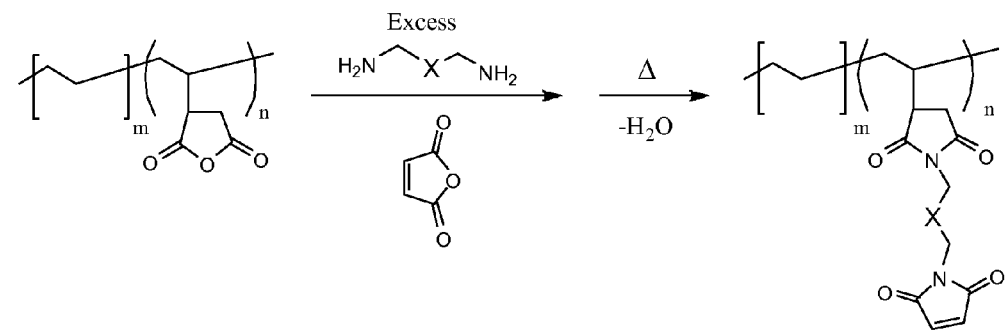
FIG. 5 illustrates the synthesis of polymaleimide of polyethylene-graft-maleic anhydride.

The Epolene® Polymers from Westlake Chemical Corporation were used for some polyethylene derivatives. The compound used was Epolene® C-19, which is a medium molecular weight highly branched polyethylene-grafted-maleic anhydride. The average molecular weight of the C-19 resin $M_W$ is approximately 13000, and the material has an acid number of 5. The material was converted to the maleimide derivative (FIG. 5) according to the following procedure.

Procedure:

Epolene® C-19 (50 g) was dissolved in 400 mL of toluene and 100 mL of NMP in a 1-L reaction flask equipped with a Teflon-coated stir bar, a Dean-Stark trap and a condenser. To the flask was added 50 mmol (26.8 g, again a large excess) of Versamine-552. The solution was heated to reflux for 2 hours to remove the small amount of water formed during the imidization process (<0.5 mL). The solution was cooled down below 50° C. and 100 mmol (9.8 g) of maleic anhydride was added to the flask along with 10 g of anhydrous methanesulfonic acid. The solution was again heated to reflux overnight to complete the maleimide synthesis. After 16 hours of reflux approximately 2 mL of water had been collected in the Dean-Stark trap. The solution was allowed to cool down and then was transferred to a dropping funnel. The solution was slowly added to 2-L of stirred acetone to precipitate the product. The mixture was filtered through a Buchner funnel and the solid was washed several times with acetone to remove any impurities. The solid was then dried in an oven at 50° C. overnight. Approximately 48 g of a white powder was recovered after drying.

While this invention has been described with respect to these specific examples, it should be clear that other modifications and variations would be possible without departing from the spirit of this invention.

What is claimed is:

1. A compound having the structure:

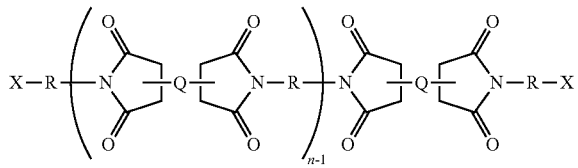

wherein:
each of R and Q is independently selected from the group consisting of a substituted or an unsubstituted aliphatic, aromatic, heteroaromatic, siloxane, unsaturated hydrocarbon, polyester, polyamide and polyurethane moieties;
X is a polymerizable or a curative moiety; and
n is an integer having the value between 1 and about 10.

2. The compound of claim 1, wherein the polymerizable moiety is selected from the group consisting of a cationic polymerizable moiety, an anionic polymerizable moiety, a ring-opening polymerizable moiety and a free radical polymerizable moiety.

3. The compound of claim 1, wherein the curative is selected from the group consisting of phenol, a phenyl ester, an anhydride, a thiol, an amino, a carboxyl, an alcohol moieties and any combination thereof.

4. The compound of claim 1, wherein the polymerizable moiety selected from the group consisting of is vinyl ether, vinyl ester, an acrylate, a methacrylate, an epoxy, an oxetane, an oxazoline, a benzoxazine, vinyl chloride, an urethane, norbornyl, maleimide, phenol, a phenyl ester, styrenic, a propargyl ether, a cyanate ester, nadimide and combinations thereof.

5. The polymer of claim 1, wherein each of R and Q is independently selected from the group consisting of:
(a) a substituted or an unsubstituted linear, branched, cyclic aliphatic and alkenyl moieties having between 2 and about 500 carbon atoms; and
(b) a substituted or an unsubstituted aromatic or heteroaromatic moieties having between 6 and about 20 carbon atoms.

6. The compound of claim 1, wherein the compound is an imide-extended bismaleimide having the structure:

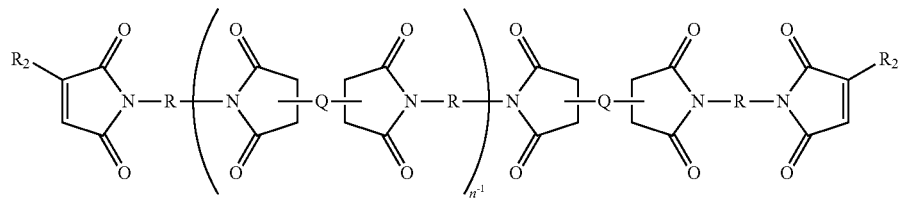

wherein:
each of R and Q is independently selected from the group consisting of a substituted or an unsubstituted aliphatic, alkenyl, aromatic, heteroaromatic and siloxane moieties; and
$R_2$ is selected from the group consisting of H and methyl, with the further proviso that the imide-extended bismaleimide is not

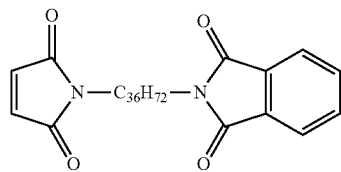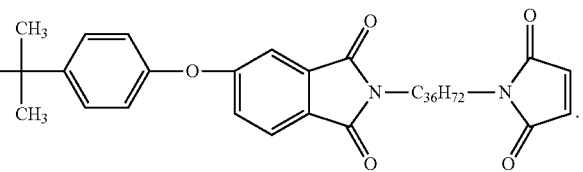

7. The compound of claim 6, wherein each of R and Q is independently selected from the group consisting of:
(a) substituted or unsubstituted linear, branched, cyclic aliphatic and alkenyl moieties having between 2 and about 500 carbon atoms;
(b) substituted or unsubstituted aromatic or heteroaromatic moieties having between 6 and about 20 carbon atoms; and
(c) substituted or unsubstituted siloxane moieties having between 2 and about 1000 silicon atoms.

8. The compound of claim 7, wherein each of R and Q is independently selected from the group consisting of substituted or unsubstituted siloxane moieties, wherein the siloxane moieties are polysiloxanes comprising repeating units selected from the group consisting of dimethylsiloxane, methylphenylsiloxane, diphenylsiloxane, methylhydrosiloxane, and combinations thereof.

9. The compound of claim 7, wherein the substituted aliphatic, alkenyl, aromatic, heteroaromatic or siloxane moieties comprise substituents selected from the group consisting of an alkyl, an alkenyl, an alkynyl, hydroxy, oxo, an alkoxy, mercapto, a cycloalkyl, a substituted cycloalkyl, a heterocyclic, a substituted heterocyclic, an aryl, a substituted aryl, a heteroaryl, a substituted heteroaryl, an aryloxy, a substituted aryloxy, a halogen, a haloalkyl, cyano, nitro, nitrone, an amino, an amido, —C(O)H, —C(O)—O—, —C(O)—, —S—, —S(O)$_2$—, —OC(O)—O—, —NR—C(O)—, —NR—C(O)—NR—, —OC(O)—NR—, wherein R is selected from the group consisting of H, a lower alkyl, an acyl, an oxyacyl, carboxyl, carbamate, sulfonyl, sulfonamide and sulfuryl.

10. An adhesive composition comprising:
(a) between 0.1 wt % and about 5 wt % of at least one curing initiator based on total weight of the composition, the curing initiator comprising a free-radical initiator or a photoinitiator; and
(b) at least one
imide-extended bismaleimide of claim 6.

* * * * *